US011124840B2

(12) United States Patent
Dua et al.

(10) Patent No.: US 11,124,840 B2
(45) Date of Patent: *Sep. 21, 2021

(54) METHODS AND COMPOSITIONS FOR CLASSIFYING DLBCL

(71) Applicant: Roche Molecular Systems, Inc., Pleasanton, CA (US)

(72) Inventors: Rajiv Dua, Manteca, CA (US); Marcel Fontecha, San Ramon, CA (US); Yan Li, Palo Alto, CA (US); Wei-min Liu, Dublin, CA (US); Christopher Santini, Pleasant Hill, CA (US); Lori Steiner, Alameda, CA (US); Yu Chuan Tai, Pleasanton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 164 days.

This patent is subject to a terminal disclaimer.

(21) Appl. No.: 16/098,019

(22) PCT Filed: May 11, 2017

(86) PCT No.: PCT/EP2017/061313
§ 371 (c)(1),
(2) Date: Oct. 31, 2018

(87) PCT Pub. No.: WO2017/194670
PCT Pub. Date: Nov. 16, 2017

(65) Prior Publication Data
US 2019/0144947 A1    May 16, 2019

Related U.S. Application Data

(60) Provisional application No. 62/336,486, filed on May 13, 2016.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2005/0079513 A1    4/2005   Levy et al.

FOREIGN PATENT DOCUMENTS

WO    2015069790 A1    5/2015
WO    2015135935 A1    9/2015

OTHER PUBLICATIONS

Care et al; PLOS One, Feb. 2013, vol. 8, e55895, pp. 1-22.*
Cai et al; PLOS one; Sep. 2010, vol. 5, e12726.*
Cai, Y.-D., et al., A Unified 35-Gene Signature for both Subtype Classification and Survival Prediction in Diffuse Large B-Cell Lymphomas, PLoS One, Sep. 13, 2010, p. e12726 (1-8), vol. 5, No. 9.
Care, M.A., et al., A Microarray Platform-Independent Classification Tool for Cell of Origin Class Allows Comparative Analysis of Gene Expression in Diffuse Large B-cell Lymphoma, PLoS One, Feb. 12, 2013, p. e55895 (1-22), vol. 8, No. 2.
International Search Report dated Jul. 21, 2017 in Application No. PCT/EP2017/061313, 15 pages.
Wright, G., et al., A gene expression-based method to diagnose clinically distinct subgroups of diffuse large B cell lymphoma, Proceedings National Academy of Sciences PNAS, Aug. 19, 2003, pp. 9991-9996, vol. 100, No. 17.

* cited by examiner

*Primary Examiner* — Jehanne S Sitton
(74) *Attorney, Agent, or Firm* — Jennifer Rosenfield; Carol Pamela Johns

(57) ABSTRACT

Provided herein are methods and compositions to classify DLBCL subtypes using quantitative RT-PCR.

23 Claims, No Drawings

Specification includes a Sequence Listing.

SEQUENCE LISTING

```
<160> NUMBER OF SEQ ID NOS: 314

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ggcagtattg acagggagga                                              20

<210> SEQ ID NO 2
<211> LENGTH: 19
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 2
tggtttaccc acaggctga                                                   19

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
ggagaaggcc aatttggaga t                                                21

<210> SEQ ID NO 4
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
acagttttta catgttttaa ttgcaacc                                         28

<210> SEQ ID NO 5
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
ggacagaaaa ggaatgctac aacta                                            25

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
cgcaatggtt agggatggtg                                                  20

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
agcttagtac agctcttgca t                                                21
```

<210> SEQ ID NO 8
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 8
tcatttgagg acaccagaac att                                              23

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 9
gcccagaaga aggaatcagt t                                                21

<210> SEQ ID NO 10
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 10
ggtttgcact tgagtgaagt c                                                21

<210> SEQ ID NO 11
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 11
accattcccc tcctaccag                                                   19

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 12
ctcacccagg tcagagttca                                                  20

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13
gacctcagga gatagcaatg t                                              21

<210> SEQ ID NO 14
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
cacttgccca atccctcg                                                  18

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
gaatggaacc tcgcagtcat                                                20

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
ggccaacttt ggtattgatg g                                              21

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
ttcgacgttt tacctcagct                                                20

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
ggcttcacac catgcatcag                                                20

<210> SEQ ID NO 19
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
gaaagaaggt gaacgggctt                                             20

<210> SEQ ID NO 20
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
gtgtgtccgc atgccttg                                               18

<210> SEQ ID NO 21
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
cctgtctgga taatcatgga gc                                          22

<210> SEQ ID NO 22
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
gctagatcca aactgtattt ccttac                                      26

<210> SEQ ID NO 23
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
cggcccaggt ttactgaac                                              19

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
tcttcttgct gagccttctc t                                           21
```

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
caggctgcat caggatgaat                                              20

<210> SEQ ID NO 26
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
cagcaggctc tcaggaca                                                18

<210> SEQ ID NO 27
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
ctctcaggct gcatcagga                                               19

<210> SEQ ID NO 28
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
cagcaggctc tcaggaca                                                18

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
acaagatcag cttctcccac                                              20

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 30
ctcgtagagt cttggaatgc a                                              21

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
caagatcagc ttctcccacg                                                20

<210> SEQ ID NO 32
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
ctcgtagagt cttggaatgc aat                                            23

<210> SEQ ID NO 33
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
aggaaccaga aacaatagaa gaaca                                          25

<210> SEQ ID NO 34
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
cgatttcaca gtggttacag ga                                             22

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
gccaaagagg aaccagaaac a                                              21

<210> SEQ ID NO 36
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
accgatttca cagtggttac a                                        21

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
cagtagggct gagatgttgg                                          20

<210> SEQ ID NO 38
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
acgtgctgaa tcatcacttc aa                                       22

<210> SEQ ID NO 39
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
ggccagtagg gctgagat                                            18

<210> SEQ ID NO 40
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
acgtgctgaa tcatcacttc aa                                       22

<210> SEQ ID NO 41
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
```

```
gactgccaaa ttaaaaaacg ttca                                           24

<210> SEQ ID NO 42
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
tttctgggta agaggcaat agtc                                            24

<210> SEQ ID NO 43
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
ggaagccaag tctttctgaa aag                                            23

<210> SEQ ID NO 44
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
gaggacttga gatttgttgc c                                              21

<210> SEQ ID NO 45
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
ggcagaagaa aatttgaaga aagaaa                                         26

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
aatgatttcc tgtgcctggt                                                20

<210> SEQ ID NO 47
<211> LENGTH: 21
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"

<400> SEQUENCE: 47
ggtggctggg atggaaaata a                                              21

<210> SEQ ID NO 48
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
ggacggtgtt cactctgct                                                 19

<210> SEQ ID NO 49
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
gaagagccac ctgcgaatc                                                 19

<210> SEQ ID NO 50
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
gctggctttt gtgacggaaa                                                20

<210> SEQ ID NO 51
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
ccacctgcga atccacac                                                  18

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
ctggcttttg tgacggaaat g                                              21

<210> SEQ ID NO 53
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
gaagagccac ctgcgaatc                                                  19

<210> SEQ ID NO 54
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
gctggctttt gtgacggaa                                                  19

<210> SEQ ID NO 55
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
ccacctgcga atccacac                                                   18

<210> SEQ ID NO 56
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
gctggctttt gtgacggaaa                                                 20

<210> SEQ ID NO 57
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
catgttgtgg acacttgcc                                                  19

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
```

```
cttcacgagg aggcttgatg                                              20

<210> SEQ ID NO 59
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
ggagcatgtt gtggacactt                                              20

<210> SEQ ID NO 60
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 60
ctcttcacga ggaggcttga                                              20

<210> SEQ ID NO 61
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 61
atggagcatg ttgtggacac                                              20

<210> SEQ ID NO 62
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 62
cgaggaggct tgatggca                                                18

<210> SEQ ID NO 63
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 63
ggactccacc atcccacaa                                               19

<210> SEQ ID NO 64
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 64
tagagtggtg agtggctctc                                            20

<210> SEQ ID NO 65
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
gtgccctgct tcatgatg                                              18

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
ctggtgtcga gagatccact c                                          21

<210> SEQ ID NO 67
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
ggctgtgcca aactcatt                                              18

<210> SEQ ID NO 68
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
gggctgtaca cccttgt                                               17

<210> SEQ ID NO 69
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69
gtgccctgct tcatgatg                                              18
```

```
<210> SEQ ID NO 70
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70
catggtactg gtgtcgagag a                                              21

<210> SEQ ID NO 71
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
gtgccctgct tcatgatg                                                  18

<210> SEQ ID NO 72
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
ccgggagtgc atggtact                                                  18

<210> SEQ ID NO 73
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
ggacaccgcc tcacagat                                                  18

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
agtgggcatg tgactgagtc                                                20

<210> SEQ ID NO 75
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 75
ggacaccgcc tcacagat                                                18

<210> SEQ ID NO 76
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76
cttcgagtgg gcatgtga                                                18

<210> SEQ ID NO 77
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
cgcctcacag atcgactc                                                18

<210> SEQ ID NO 78
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
gcagtgcgac ttcgagtg                                                18

<210> SEQ ID NO 79
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
accgtcttcg caggacac                                                18

<210> SEQ ID NO 80
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
gggcatgtga ctgagtctg                                               19

<210> SEQ ID NO 81
<211> LENGTH: 19
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 81
ggcgactgga cttacgagg                                                       19

<210> SEQ ID NO 82
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 82
ccaggaattc cttcctcttg g                                                    21

<210> SEQ ID NO 83
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
tcctggatga cttgttcagc                                                      20

<210> SEQ ID NO 84
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
aggacctgtt tggccatgat                                                      20

<210> SEQ ID NO 85
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
acgtccatca ccagtgca                                                        18

<210> SEQ ID NO 86
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
cttctcacac tcgtaggggt                                                      20
```

<210> SEQ ID NO 87
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
acgtccatca ccagtgca                                                    18

<210> SEQ ID NO 88
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 88
cccgcttctc acactcgta                                                   19

<210> SEQ ID NO 89
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
cagctgccca tgagcattc                                                   19

<210> SEQ ID NO 90
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
tcaggttcac agcagagtcc                                                  20

<210> SEQ ID NO 91
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 91
cagctgccca tgagcattc                                                   19

<210> SEQ ID NO 92
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
cgtcaggttc acagcagag                                          19

<210> SEQ ID NO 93
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
agcatgtcgg tggagatcaa                                         20

<210> SEQ ID NO 94
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 94
ttgggagcag aggttggc                                           18

<210> SEQ ID NO 95
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
atcagcatgt cggtggagat                                         20

<210> SEQ ID NO 96
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
tttgttggga gcagaggttg                                         20

<210> SEQ ID NO 97
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
aggacatcca accctacatg c                                       21

<210> SEQ ID NO 98
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
gaagacctct tcttcgcact                                              20

<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
cttcattgct ctgtgtgcca                                              20

<210> SEQ ID NO 100
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
tgctcccaca cttccagtt                                               19

<210> SEQ ID NO 101
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
cttcattgct ctgtgtgcca                                              20

<210> SEQ ID NO 102
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
ccacacttcc agttgcgatc                                              20

<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
gactgagctg ctggctaaga                                              20
```

<210> SEQ ID NO 104
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
gagcaccgcc tcaatctg                                                   18

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
ggacatccaa ccctacatgc                                                 20

<210> SEQ ID NO 106
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
agagggaaga cctcttcttc g                                               21

<210> SEQ ID NO 107
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
ggacatccaa ccctacatgc                                                 20

<210> SEQ ID NO 108
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
ggaagacctc ttcttcgcac t                                               21

<210> SEQ ID NO 109
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 109
cttcattgct ctgtgtgcca                                              20

<210> SEQ ID NO 110
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
ctgctcccac acttccagt                                               19

<210> SEQ ID NO 111
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
accttcattg ctctgtgtgc                                              20

<210> SEQ ID NO 112
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
gctcccacac ttccagttg                                               19

<210> SEQ ID NO 113
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 113
aaggacctgc ctctgtcg                                                18

<210> SEQ ID NO 114
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
tctcctctgc catcttcagg                                              20

<210> SEQ ID NO 115
<211> LENGTH: 18

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
ccaaggacct gcctctgt                                                   18

<210> SEQ ID NO 116
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 116
ctcctctgcc atcttcaggg                                                 20

<210> SEQ ID NO 117
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 117
ccaaggacct gcctctgtc                                                  19

<210> SEQ ID NO 118
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
tctcctctgc catcttcagg                                                 20

<210> SEQ ID NO 119
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
ccaaggacct gcctctgtc                                                  19

<210> SEQ ID NO 120
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
```
ctcctctgcc atcttcaggg					20

<210> SEQ ID NO 121
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
caaggacctg cctctgtcg					19

<210> SEQ ID NO 122
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
tctcctctgc catcttcagg					20

<210> SEQ ID NO 123
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 123
ccaaggacct gcctctgt					18

<210> SEQ ID NO 124
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 124
ctctgccatc ttcaggggat					20

<210> SEQ ID NO 125
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 125
aaggacctgc ctctgtcg					18

<210> SEQ ID NO 126
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 126
tgctctcctc tgccatcttc                                              20

<210> SEQ ID NO 127
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
ccaaggacct gcctctgtc                                               19

<210> SEQ ID NO 128
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 128
ctctgccatc ttcagggggat                                             20

<210> SEQ ID NO 129
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 129
aaaccagcaa ccagcacttt                                              20

<210> SEQ ID NO 130
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 130
gaggagctcc aagggtcac                                               19

<210> SEQ ID NO 131
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 131
caaccagcac tttccctagc                                              20

<210> SEQ ID NO 132
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132
ccactggagg agctccaag                                                      19

<210> SEQ ID NO 133
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133
acttcccctg acctgaacc                                                      19

<210> SEQ ID NO 134
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 134
gagacactct gccctgtag                                                     20

<210> SEQ ID NO 135
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 135
cgacttcccc tgacctgaa                                                      19

<210> SEQ ID NO 136
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 136
gagacactct gccctgtag                                                     20

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 137
```
gcaaccagca ctttccctag                                                  20

<210> SEQ ID NO 138
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 138
attcatccca ctggaggagc                                                  20

<210> SEQ ID NO 139
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 139
tggccgtcat cctcagtc                                                    18

<210> SEQ ID NO 140
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 140
cctcccttct tttcagacac g                                                21

<210> SEQ ID NO 141
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 141
gtggccgtca tcctcagtc                                                   19

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 142
tcttttcaga cacgcagctt                                                  20

<210> SEQ ID NO 143
<211> LENGTH: 18
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 143
gtggccgtca tcctcagt                                                 18

<210> SEQ ID NO 144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 144
tcttttcaga cacgcagctt                                               20

<210> SEQ ID NO 145
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 145
tcaagtcaaa aattccaaat gaacac                                        26

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 146
tggaagtttc atggcactga                                               20

<210> SEQ ID NO 147
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
taccagccag tccagacac                                                19

<210> SEQ ID NO 148
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 148
tcggataaac agaacgtcct t                                             21
```

```
<210> SEQ ID NO 149
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 149
ggcttcagga actcaatgaa ga                                              22

<210> SEQ ID NO 150
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 150
caggacttct actgtctttt cca                                             23

<210> SEQ ID NO 151
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 151
ggcttcagga actcaatgaa ga                                              22

<210> SEQ ID NO 152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 152
ggcgttccag gacttctact                                                 20

<210> SEQ ID NO 153
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 153
gggaatgata tggtgttctg tga                                             23

<210> SEQ ID NO 154
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 154
ccttctggga ccttgagga                                                19

<210> SEQ ID NO 155
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 155
actaaatggg ctcatgtcag c                                             21

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 156
atcggttcca tcctctcagg                                               20

<210> SEQ ID NO 157
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 157
tgagaatgtt tatgcatcta cgc                                           23

<210> SEQ ID NO 158
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 158
agcttctctc gtctgcttat ca                                            22

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 159
ggtttgcaag tccagcttct                                               20

<210> SEQ ID NO 160
<211> LENGTH: 22
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 160
tggtgggtaa aacagtgagt tt                                              22

<210> SEQ ID NO 161
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 161
gccaccagga acacccat                                                   18

<210> SEQ ID NO 162
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 162
ggtccaggag gtactgcatt                                                 20

<210> SEQ ID NO 163
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 163
acatgtatac tttaatgaat gcagtacc                                        28

<210> SEQ ID NO 164
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 164
tgggaccatc tgacccag                                                   18

<210> SEQ ID NO 165
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 165
aacatgtata ctttaatgaa tgcagtacc                                       29
```

<210> SEQ ID NO 166
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 166
atgggaccat ctgacccag                                              19

<210> SEQ ID NO 167
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 167
gccaccagga acacccat                                               18

<210> SEQ ID NO 168
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 168
ccaggaggta ctgcattcat t                                           21

<210> SEQ ID NO 169
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 169
gccaccagga acacccat                                               18

<210> SEQ ID NO 170
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 170
gtccaggagg tactgcattc a                                           21

<210> SEQ ID NO 171
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

```
<400> SEQUENCE: 171
acatgtatac tttaatgaat gcagtacc                                    28

<210> SEQ ID NO 172
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 172
atgggaccat ctgacccag                                              19

<210> SEQ ID NO 173
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 173
gccaccagga acacccat                                               18

<210> SEQ ID NO 174
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 174
tccaggaggt actgcattca tt                                          22

<210> SEQ ID NO 175
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
gccaccagga acacccat                                               18

<210> SEQ ID NO 176
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 176
taggtccagg aggtactgca                                             20

<210> SEQ ID NO 177
<211> LENGTH: 22
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 177
aacagtatta cctggtagct cc                                            22

<210> SEQ ID NO 178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 178
agggcacata aaccacctga                                               20

<210> SEQ ID NO 179
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 179
atcgatccca cctgtaacgt                                               20

<210> SEQ ID NO 180
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 180
caggtaatac tgttcacaca gca                                           23

<210> SEQ ID NO 181
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 181
gaacagtatt acctggtagc tcc                                           23

<210> SEQ ID NO 182
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 182
gagggcacat aaaccacctg                                               20
```

<210> SEQ ID NO 183
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 183
atcgatccca cctgtaacgt                                              20

<210> SEQ ID NO 184
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 184
ccaggtaata ctgttcacac agc                                          23

<210> SEQ ID NO 185
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 185
gaacagtatt acctggtagc tcc                                          23

<210> SEQ ID NO 186
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 186
gggcacataa accacctgaa                                              20

<210> SEQ ID NO 187
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 187
aacagtatta cctggtagct cc                                           22

<210> SEQ ID NO 188
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 188
gtgagggcac ataaaccacc                                              20

<210> SEQ ID NO 189
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 189
atcgatccca cctgtaacgt                                              20

<210> SEQ ID NO 190
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 190
caggtaatac tgttcacaca gc                                           22

<210> SEQ ID NO 191
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 191
tcgccgctct ccatcaaa                                                18

<210> SEQ ID NO 192
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 192
gcacaggaag ttcctttcgt a                                            21

<210> SEQ ID NO 193
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 193
gaagatctct gatgagaaga accg                                         24

<210> SEQ ID NO 194
<211> LENGTH: 22

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 194
gcttcccggt cattctttag tt                                    22

<210> SEQ ID NO 195
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 195
tgccataaag cgcactgac                                        19

<210> SEQ ID NO 196
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 196
ggcaataaaa tccactgatg gga                                   23

<210> SEQ ID NO 197
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 197
gtactatctt aggaccgagt tagag                                 25

<210> SEQ ID NO 198
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 198
gccatccttc tcccttcgtt                                       20

<210> SEQ ID NO 199
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 199

-continued atgccataaa gcgcactgac                                               20

<210> SEQ ID NO 200
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 200
ggcaataaaa tccactgatg gg                                            22

<210> SEQ ID NO 201
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 201
tgtactatct taggaccgag ttagag                                        26

<210> SEQ ID NO 202
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 202
gccatccttc tcccttcgtt                                               20

<210> SEQ ID NO 203
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 203
agatgtacta tcttaggacc gagt                                          24

<210> SEQ ID NO 204
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 204
ccatccttct cccttcgttt                                               20

<210> SEQ ID NO 205
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 205
gccataaagc gcactgacaa                                                 20

<210> SEQ ID NO 206
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 206
ggcaataaaa tccactgatg gg                                              22

<210> SEQ ID NO 207
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 207
gtactatctt aggaccgagt tagag                                           25

<210> SEQ ID NO 208
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208
ccatccttct cccttcgttt c                                               21

<210> SEQ ID NO 209
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 209
aagacttacc tgcggaaaac g                                               21

<210> SEQ ID NO 210
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 210
tggcttcttt ctctcctgct                                                 20

<210> SEQ ID NO 211
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 211
agacttacct gcggaaaacg                                                    20

<210> SEQ ID NO 212
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 212
ttggcttctt tctctcctgc                                                    20

<210> SEQ ID NO 213
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 213
aagacttacc tgcggaaaac g                                                  21

<210> SEQ ID NO 214
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 214
cttggcttct ttctctcctg c                                                  21

<210> SEQ ID NO 215
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 215
gacttacctg cggaaaacgg                                                    20

<210> SEQ ID NO 216
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 216
```

```
ttggcttctt tctctcctgc                                              20

<210> SEQ ID NO 217
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 217
agacttacct gcggaaaacg                                              20

<210> SEQ ID NO 218
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 218
tggcttcttt ctctcctgct                                              20

<210> SEQ ID NO 219
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 219
aagacttacc tgcggaaaac g                                            21

<210> SEQ ID NO 220
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 220
ttggcttctt tctctcctgc                                              20

<210> SEQ ID NO 221
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 221
caacgagagt gacagcagtc                                              20

<210> SEQ ID NO 222
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 222
ggctcttctt tgacgtgtac a                                              21

<210> SEQ ID NO 223
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 223
caacgagagt gacagcagtc                                                20

<210> SEQ ID NO 224
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 224
gggctcttct ttgacgtgta                                                20

<210> SEQ ID NO 225
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 225
cgcctactgc acacctctc                                                 19

<210> SEQ ID NO 226
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 226
catggaagcg gtagtgtata gag                                            23

<210> SEQ ID NO 227
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 227
cgcctactgc acacctctc                                                 19
```

```
<210> SEQ ID NO 228
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 228
ccatggaagc ggtagtgtat ag                                              22

<210> SEQ ID NO 229
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 229
cgcctactgc acacctctc                                                  19

<210> SEQ ID NO 230
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 230
ccatggaagc ggtagtgta                                                  19

<210> SEQ ID NO 231
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 231
agagcagcca cgcctact                                                   18

<210> SEQ ID NO 232
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 232
catggaagcg gtagtgtata gag                                             23

<210> SEQ ID NO 233
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 233
cgaaggccac aaaagatca                                                19

<210> SEQ ID NO 234
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 234
gcattgagag gtgtgcagta                                               20

<210> SEQ ID NO 235
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 235
atggacagtg gatgaagtag aattc                                         25

<210> SEQ ID NO 236
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 236
gctgctctgc atgtttttaa taa                                           23

<210> SEQ ID NO 237
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 237
tcttcccatt tcagacagca                                               20

<210> SEQ ID NO 238
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 238
gaggactgga agcactgttt                                               20

<210> SEQ ID NO 239
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 239
tcttcccatt tcagacagca                                                      20

<210> SEQ ID NO 240
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 240
ggaggactgg aagcactgt                                                       19

<210> SEQ ID NO 241
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 241
agcaagagtc tgggtcttct a                                                    21

<210> SEQ ID NO 242
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 242
gtttcagtca ctgggctgac                                                      20

<210> SEQ ID NO 243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 243
agcaagagtc tgggtcttct                                                      20

<210> SEQ ID NO 244
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 244
tttcagtcac tgggctgac                                                       19
```

-continued

```
<210> SEQ ID NO 245
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 245
acagaaacct gtagctgttc c                                              21

<210> SEQ ID NO 246
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 246
gctctttggc taatagttct gca                                            23

<210> SEQ ID NO 247
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 247
acagaaacct gtagctgttc c                                              21

<210> SEQ ID NO 248
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 248
gctctttggc taatagttct gc                                             22

<210> SEQ ID NO 249
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 249
aattctcagc tggcaggttc                                                20

<210> SEQ ID NO 250
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 250
gattcaaagt cttttcggac aca                                          23

<210> SEQ ID NO 251
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 251
tgggctcctc ctagatttca                                              20

<210> SEQ ID NO 252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 252
agaaaaaatt ctgggctgcc a                                            21

<210> SEQ ID NO 253
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 253
caagggctgc aatcccacac atcttgc                                      27

<210> SEQ ID NO 254
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 254
aagtcttcag ggtccgattg gaaaccaaca                                   30

<210> SEQ ID NO 255
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 255
aggcatttat atgagtccag agaatccagc tttgg                             35

<210> SEQ ID NO 256
<211> LENGTH: 23
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 256
aggtgcaccc gagcctctga cag                                            23

<210> SEQ ID NO 257
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 257
caaaagattt gtacacaggg acattgctgc tcg                                 33

<210> SEQ ID NO 258
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 258
taacggacaa gggctgcaat cccacac                                        27

<210> SEQ ID NO 259
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 259
tgacccaagt atggaagaga atggtgttga acg                                 33

<210> SEQ ID NO 260
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 260
agaggcccaa ggcacaagtc cag                                            23

<210> SEQ ID NO 261
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 261
acatgcttca ggagactctg tggtttccc                                      29
```

<210> SEQ ID NO 262
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 262
agccatcaat caggaaagcc gggttagta                                    29

<210> SEQ ID NO 263
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 263
gcttctctaa actccaagcc atcttctcta cgaagag                           37

<210> SEQ ID NO 264
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 264
gtgggatgtc tcttcagttt atgacacaat agcttcc                           37

<210> SEQ ID NO 265
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 265
actattagag tctttaacac ctctgtgtga agatgaca                          38

<210> SEQ ID NO 266
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 266
aggagagaaa ccttaccatt gtgagaagtg taacct                            36

<210> SEQ ID NO 267
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic probe"

<400> SEQUENCE: 267
ggaagtttat taaggccagt gaagcagaga tggttt                36

<210> SEQ ID NO 268
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 268
aataacatcg ttaacaggtc catgacgggc tc                    32

<210> SEQ ID NO 269
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 269
acagatcgac tccaggtggc catcaaag                         28

<210> SEQ ID NO 270
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 270
gctggtcccc cttgtcagac tcagt                            25

<210> SEQ ID NO 271
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 271
ctacactgac tttgatggga caagggtgta ca                    32

<210> SEQ ID NO 272
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 272
tcacatgccc actcgaagtc gca                              23

<210> SEQ ID NO 273
<211> LENGTH: 27

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 273
ctgactttga tgggacaagg gtgtaca                                         27

<210> SEQ ID NO 274
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 274
ctggtgccct gcttcatgat gaacc                                           25

<210> SEQ ID NO 275
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 275
cactgacttt gatgggacaa gggtg                                           25

<210> SEQ ID NO 276
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 276
agcagtttaa gcagctctac gaactcgacg                                      30

<210> SEQ ID NO 277
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 277
tgcagaagcg agggacacct gtga                                            24

<210> SEQ ID NO 278
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 278
``` cctgcggac ccaatacatg aagtacct                                         28

<210> SEQ ID NO 279
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 279
caacagccaa gcctccgaaa gccg                                            24

<210> SEQ ID NO 280
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 280
cggcatcatg tacacaggag ttctgtttgc tca                                  33

<210> SEQ ID NO 281
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 281
agtttgccat gtacccaccg tcga                                            24

<210> SEQ ID NO 282
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 282
ctttaagttt gccatgtacc caccgtcg                                        28

<210> SEQ ID NO 283
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 283
ttgccatgta cccaccgtcg atgat                                           25

<210> SEQ ID NO 284
<211> LENGTH: 28
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic probe"

<400> SEQUENCE: 284
ttctattgcc cagtttcccc agccagaa                                        28

<210> SEQ ID NO 285
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 285
ctcttctatt gcccagtttc cccagccag                                       29

<210> SEQ ID NO 286
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 286
ctcctcttct attgcccagt ttccccagc                                       29

<210> SEQ ID NO 287
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 287
tccttcttca tgcaagatgg ccatcacagc                                      30

<210> SEQ ID NO 288
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 288
aggaccctta cagaggcatg ccacc                                           25

<210> SEQ ID NO 289
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 289
tggagcagca agtccgagaa aggaatctga a                                    31

<210> SEQ ID NO 290
```

```
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 290
agaaacctgc tgaggtattc cggaaggac                                            29

<210> SEQ ID NO 291
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 291
cacagccttc tctcaggatt atagctgaga aggt                                      34

<210> SEQ ID NO 292
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 292
cttgcagaaa tgggttgtgg gccagtt                                              27

<210> SEQ ID NO 293
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 293
tgtgtgcatc aggcctgcta tggc                                                 24

<210> SEQ ID NO 294
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 294
tgtggatccc agaggtcagc attgcttg                                             28

<210> SEQ ID NO 295
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 295
```
aggacctgga gagggtccga aatctgt                                    27

<210> SEQ ID NO 296
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 296
ccaagaaatt gatgcagggc ttcctttgac aaatg                           35

<210> SEQ ID NO 297
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 297
catgcctagt ccagcagatt caaccaactc t                               31

<210> SEQ ID NO 298
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 298
cctggaccta acagacctaa ttttccaatg gg                              32

<210> SEQ ID NO 299
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 299
ttgaagaatt caatgccaaa gcgccagaca aa                              32

<210> SEQ ID NO 300
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 300
cggatgtggt gaaagatgca tatgaaacag cc                              32

<210> SEQ ID NO 301
<211> LENGTH: 34
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic probe"

<400> SEQUENCE: 301
caattcctgg acttcgggag agataatgca tgtg                                34

<210> SEQ ID NO 302
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 302
tgcttcccag aagcaaaagg ttattgaaga gagg                                34

<210> SEQ ID NO 303
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 303
taactgttcc tgcaaaaggc tctgagtttc tgg                                 33

<210> SEQ ID NO 304
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 304
cggcttcata aacaacaagg agaaatgctg cgc                                 33

<210> SEQ ID NO 305
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 305
cgaagactga ggagagtcca gcctct                                         26

<210> SEQ ID NO 306
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 306
aacgaagact gaggagagtc cagcctc                                        27
```

```
<210> SEQ ID NO 307
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 307
aagactgagg agagtccagc ctctgatg                                          28

<210> SEQ ID NO 308
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 308
ccacaaaaga tcagtggtaa cccttccc                                          28

<210> SEQ ID NO 309
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 309
tcctatgcaa gccgtgcatc c                                                 21

<210> SEQ ID NO 310
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 310
tgtagaagat gttcagcgtg cagggctt                                          28

<210> SEQ ID NO 311
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 311
catacagtgg ctatgaaggt tgtgctgtgt taca                                   34

<210> SEQ ID NO 312
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

```
<400> SEQUENCE: 312
tgcagctcct ctaagagtgt cacttatgag cc                                    32

<210> SEQ ID NO 313
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 313
tgcagctggc tcgatagtcg taaatgaaga                                       30

<210> SEQ ID NO 314
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 314
ttcatccacc actcaagagg gaccttgtg                                        29
```

METHODS AND COMPOSITIONS FOR CLASSIFYING DLBCL

CROSS-REFERENCE TO RELATED APPLICATIONS

This patent application is a US National Phase application claiming priority to WO2017194670 (PCT/EP2017/061313), filed 11 May 2017, which claims priority to U.S. Provisional Patent Application No. 62/336,486, filed 13 May 2016, the disclosures of which are incorporated by reference herein in their entireties.

BACKGROUND OF THE INVENTION

Diffuse Large B-Cell Lymphoma (DLBCL) comprises 30-35% of all Non-Hodgkin lymphoma. DLBCL is biologically aggressive, but can be cured in >50% of the cases. However, up to one third of the patients develop resistance and are refractory to the treatments. The standard treatment is chemotherapy CHOP or chemotherapy+Rituxamab (R-CHOP). DLBCL can be classified into three different molecular cell-of-origin (COO) subtypes: germinal center B-cell (GCB), activated B-cell (ABC), and primary mediastinal B-cell lymphoma (PMBCL). Retrospective analysis by the Lymphoma/Leukemia molecular profiling project demonstrated that DLBCL patients with GCB subtype have better prognosis than those with ABC subtype when treated with R-CHOP, and drug candidates to improve ABC subtype prognosis are in development.

Current methods for distinguishing GCB and ABC subtypes include immunohistochemistry (IHC) and gene expression profiling. IHC and gene expression profiling technologies are time consuming, and have additional drawbacks for subtype classification. For example, gene expression technology uses frozen samples and not the formaldehyde fixed paraffin embedded tissue (FFPET) specimens that are typically collected in clinical laboratories. Nanostring Technologies (Seattle, Wash.) has developed a gene expression profiling signature that classifies DLBCL subtypes using FFPET samples, but the Nanostring platform is not widely adopted in the marketplace and it is expensive. IHC also uses FFPET samples but shows high assay variability across laboratories.

SUMMARY OF THE INVENTION

Provided herein are methods and compositions for determining diffuse large B cell lymphoma (DLBCL) subtype and treating DLBCL patients. Provided herein are methods and compositions for determining diffuse large B cell lymphoma (DLBCL) subtype and treating DLBCL patients. In some embodiments, provided are methods of identifying an individual with DLBCL comprising: (a) obtaining a sample from the individual (DLBCL sample); (b) detecting by qRT-PCR the expression of GCB markers ZNF318, PDK3, HMGN1, PTK2, SSBP2, BCL6, and/or LRMP in the DLBCL sample; (c) detecting by qRT-PCR the expression of ABC markers ARID3A, CCND2, FOXP1, KIAA0226L, JADE3, PIM2, TCF4, and/or FAM46C in the DLBCL sample and the control sample; and (d) detecting by qRT-PCR the expression of a control gene (e.g., internal control) in the DLBCL sample; wherein the ratio of GCB marker expression to ABC marker expression being higher than a GCB threshold value in said individual's sample indicates sensitivity of said individual to the administration of R-CHOP (rituximab or etoposide; cyclophosphamide; doxorubicin; vincristine; and prednisolone). Some embodiments, if the ratio of ABC marker expression to GCB marker expression is higher than an ABC threshold value in the individual's sample indicate sensitivity of the individual to an alternative administration. In some embodiments, the method further comprises adjusting the level of expression detected for the genes in steps (b) and (c) based on the expression detected of the control gene in (d). In some embodiments, the administration is provided directly to the patient.

In some embodiments, provided are methods of providing treatment for an individual with DLBCL comprising: (a) obtaining a sample from the individual (DLBCL sample); (b) detecting by qRT-PCR the expression of GCB markers ZNF318, PDK3, HMGN1, PTK2, SSBP2, BCL6, and/or LRMP in the DLBCL sample; (c) detecting by qRT-PCR the expression of ABC markers ARID3A, CCND2, FOXP1, KIAA0226L, JADE3, PIM2, TCF4, and/or FAM46C in the DLBCL sample and the control sample; (d) detecting by qRT-PCR the expression of a control gene (e.g., internal control) in the DLBCL sample; and (e) providing treatment for the individual. In some embodiments, the treatment comprises administration of R-CHOP (rituximab or etoposide; cyclophosphamide; doxorubicin; vincristine; and prednisolone) if the ratio of GCB marker expression to ABC marker expression is higher than a GCB threshold value. In some embodiments, the treatment comprises an alternative therapy if the ratio of ABC marker expression to GCB marker expression is higher than an ABC threshold value. In some embodiments, the method further comprises adjusting the level of expression detected for the genes in steps (b) and (c) based on the expression detected of the control gene in (d). In some embodiments, the treatment is provided directly to the patient.

In some embodiments, 1, 2, 3, 4, 5, or 6 GCB markers are detected in step (b) in any combination. In some embodiments, all 7 GCB markers are detected in step (b). In some embodiments, 1, 2, 3, 4, 5, 6, or 7 ABC markers are detected in step (c) in any combination. In some embodiments, all 8 ABC markers are detected in step (c). In some embodiments, step (b) comprises detecting the expression of ZNF318, SSBP2, and PTK2. In some embodiments, step (c) comprises detecting the expression of CCND2, FOXP1, and JADE3.

In some embodiments, the methods further comprise carrying out steps (b)-(d) on a GCB positive control, and the result used to set the GCB threshold value. In some embodiments, the GCB positive control comprises 51-100% known GCB sample, e.g., 55-85%, 55-65%, 60-70% known GCB sample. In some embodiments, the remaining GCB positive control is comprised of known ABC sample. In some embodiments, the method further comprises carrying out steps (b)-(d) on an ABC positive control, and the result used to set the ABC threshold value. In some embodiments, the ABC positive control comprises 51-100% known ABC sample, e.g., 55-85%, 55-65%, 60-70% known ABC sample. In some embodiments, the remaining ABC positive control is comprised of known GCB sample. In some embodiments, the method further comprises carrying out steps (b)-(d) on a negative control sample, e.g., a sample lacking nucleic acids, a non-cancer sample, or a sample substantially lacking the recited ABC and GCB marker nucleic acids.

In some embodiments, the sample is from lung biopsy (e.g., tumor tissue) or bronchoalveolar lavage. In some embodiments, the sample is formalin-fixed paraffin embedded tissue (FFPET), e.g., from a tumor sample, either in the lung or metastasized. In some embodiments, the sample is blood, plasma, serum, urine, mucous, mucosal tissue, or saliva.

In some embodiments, the detecting of (b) and (c) are carried out in multiplex in multiple vessels. For example, the detecting of (b) can be carried out in 1-6 vessels, with each of the GCB markers detected using a different label for each GCB marker probe, or using the same label on two or more GCB marker probes. Similarly, the detecting of (c) can be carried out in 1-7 vessels, with each of the ABC markers detected using a different label for each ABC marker probe, or using the same label on two or more ABC marker probes. In some embodiments, each GCB and ABC marker is individually detected. In some embodiments, the detecting of (b) is carried out in a single vessel for each sample. In some embodiments, the detecting of (c) is carried out in a single vessel for each sample. In some embodiments, the detecting of (d) is carried out in the same vessel(s) as the detecting of (b) and (c).

In some embodiments, the alternative administration or therapy includes a BTK inhibitor, SYK inhibitor, NFkB inhibitor, or immunomodulatory agent. In some embodiments, the alternative administration or therapy comprises R-CHOP, alone or in combination with a BTK inhibitor, SYK inhibitor, NFkB inhibitor, or immunomodulatory agent.

Further provided are methods for determining the cell of origin (COO) subtype for an individual with DLBCL comprising (a) obtaining a sample from the individual (DLBCL sample); (b) detecting by qRT-PCR the expression of GCB markers ZNF318, PDK3, HMGN1, PTK2, SSBP2, BCL6, and/or LRMP in the DLBCL sample; (c) detecting by qRT-PCR the expression of ABC markers ARID3A, CCND2, FOXP1, KIAA0226L, JADE3, PIM2, TCF4, and/or FAM46C in the DLBCL sample; (d) detecting by qRT-PCR the expression of a control gene in the DLBCL sample; and (e) determining that the COO subtype of the individual is (i) germinal center B cell (GCB) if the ratio of GCB marker expression to ABC marker expression is higher than a GCB threshold value, or (ii) activated B cell (ABC) if the ratio of ABC marker expression to GCB marker expression is higher than an ABC threshold value. In some embodiments, the method further comprises adjusting the level of expression detected for the genes in steps (b) and (c) based on the expression detected of the control gene in (d).

In some embodiments, 1, 2, 3, 4, 5, or 6 GCB markers are detected in step (b) in any combination. In some embodiments, all 7 GCB markers are detected in step (b). In some embodiments, 1, 2, 3, 4, 5, 6, or 7 ABC markers are detected in step (c) in any combination. In some embodiments, all 8 ABC markers are detected in step (c). In some embodiments, step (b) comprises detecting the expression of ZNF318, SSBP2, and PTK2. In some embodiments, step (c) comprises detecting the expression of CCND2, FOXP1, and JADE3.

In some embodiments, the methods further comprise carrying out steps (b)-(d) on a GCB positive control, and the result used to set the GCB threshold value. In some embodiments, the GCB positive control comprises 51-100% known GCB sample, e.g., 55-85%, 55-65%, 60-70% known GCB sample. In some embodiments, the remaining GCB positive control is comprised of known ABC sample. In some embodiments, the method further comprises carrying out steps (b)-(d) on an ABC positive control, and the result used to set the ABC threshold value. In some embodiments, the ABC positive control comprises 51-100% known ABC sample, e.g., 55-85%, 55-65%, 60-70% known ABC sample.

In some embodiments, the remaining ABC positive control is comprised of known GCB sample. In some embodiments, the method further comprises carrying out steps (b)-(d) on a negative control sample.

In some embodiments, the sample is from lung biopsy (e.g., tumor tissue) or bronchoalveolar lavage. In some embodiments, the sample is formalin-fixed paraffin embedded tissue (FFPET), e.g., from a tumor sample, either in the lung or metastasized. In some embodiments, the sample is blood, plasma, serum, urine, mucous, mucosal tissue, or saliva.

In some embodiments, the detecting of (b) and (c) are carried out in multiplex in multiple vessels. For example, the detecting of (b) can be carried out in 1-6 vessels, with each of the GCB markers detected using a different label for each GCB marker probe, or using the same label on two or more GCB marker probes. Similarly, the detecting of (c) can be carried out in 1-7 vessels, with each of the ABC markers detected using a different label for each ABC marker probe, or using the same label on two or more ABC marker probes. In some embodiments, each GCB and ABC marker is individually detected. In some embodiments, the detecting of (b) is carried out in a single vessel for each sample. In some embodiments, the detecting of (c) is carried out in a single vessel for each sample. In some embodiments, the detecting of (d) is carried out in the same vessel(s) as the detecting of (b) and (c).

In some embodiments, the method further comprises providing treatment for the individual depending on the COO subtype.

Further provided are kits for determining the COO subtype of an individual with DLBCL. In some embodiments, the kit comprises (a) a mixture comprising a primer set and a fluorescently labeled probe that specifically amplifies and detects at least one of GCB marker ZNF318, PDK3, HMGN1, PTK2, SSBP2, BCL6, and LRMP gene products (e.g., 2, 3, 4, 5, 6, or all 7); and (b) a mixture comprising a primer set and a fluorescently labeled probe that specifically amplifies and detects at least one of ABC marker ARID3A, CCND2, FOXP1, KIAA0226L, JADE3, PIM2, TCF4, and FAM46C gene products (e.g., 2, 3, 4, 5, 6, 7, or all 8). In some embodiments, the kit includes primer sets and probes to specifically amplify and detect all 7 GCB markers and all 8 ABC markers. In some embodiments, mixture (a) comprises a primer set and a fluorescently labeled probe that specifically amplifies and detects ZNF318, SSBP2, and PTK2. In some embodiments, mixture (b) comprises a primer set and a fluorescently labeled probe that specifically amplifies and detects CCND2, FOXP1, and JADE3. In some embodiments, the mixtures of (a) and (b) each further comprise a primer set and a fluorescently labeled probe that specifically amplifies and detects a control gene product, wherein the fluorescently labeled probe that specifically detects the control gene product is differently labeled than the fluorescently labeled probes in mixture (a) and mixture (b). In some embodiments, the fluorescently labeled probes in mixture (a) are all labeled with the same fluorescent label. In some embodiments, the fluorescently labeled probes in mixture (b) are all labeled with the same fluorescent label.

In some embodiments, the kit comprises a plurality of mixtures that comprise a primer set and a fluorescently labeled probe that specifically amplifies and individually detects (i) each of GCB marker ZNF318, PDK3, HMGN1, PTK2, SSBP2, BCL6, and LRMP gene products; (ii) each of ABC marker ARID3A, CCND2, FOXP1, KIAA0226L, JADE3, PIM2, TCF4, and FAM46C gene products; and (iii) a control gene product, wherein the primer set and fluorescently labeled probe that specifically amplifies and individually detects the control gene product are present in each of the plurality of mixtures. In some embodiments, the kit comprises 3-15 mixtures, e.g., 5 mixtures. In some embodiments, the kit comprises a plurality of mixtures that comprise a primer set and a fluorescently labeled probe that specifically amplifies and individually detects (i) each of ZNF318, PDK2, and SSBP2; (ii) each of CCND2, FOXP1, and JADE3; and (iii) a control gene product, wherein the primer set and fluorescently labeled probe that specifically amplifies and individually detects the control gene product are present in each of the plurality of mixtures.

In some embodiments, the kit further comprises reverse transcriptase and/or thermostable DNA polymerase. In some embodiments, the kit further comprises an enzyme with reverse transcriptase and DNA polymerase activity. In some embodiments, the kit further comprises at least one control sample, e.g., an ABC positive control and/or GCB positive control, as described herein. In some embodiments, the kit further includes a negative control (e.g., non-cancer sample).

In some embodiments, the primer set that specifically amplifies ZNF318 is a forward and reverse primer having sequences selected from SEQ ID NOs:193-208, and the sequence of the probe that individually detects ZNF318 is selected from SEQ ID NOs:302-304. In some embodiments, the sequence of the probe that individually detects ZNF318 is SEQ ID NO:304. In some embodiments, the primer set that specifically amplifies PDK3 is a forward and reverse primer having sequences selected from SEQ ID NOs:177-192, and the sequence of the probe that individually detects PDK3 is selected from SEQ ID NOs:299-301. In some embodiments, the sequence of the probe that individually detects PDK3 is SEQ ID NO:300. In some embodiments, the primer set that specifically amplifies HMGN1 is a forward and reverse primer having sequences selected from SEQ ID NOs:209-220, and the sequence of the probe that individually detects HMGN1 is selected from SEQ ID NOs:305-307. In some embodiments, the sequence of the probe that individually detects HMGN1 is SEQ ID NO:305 In some embodiments, the primer set that specifically amplifies PTK2 is a forward and reverse primer having sequences selected from SEQ ID NOs:1-24, and the sequence of the probe that individually detects PTK2 is selected from SEQ ID NOs:253-258. In some embodiments, the sequence of the probe that individually detects PTK2 is SEQ ID NO:253. In some embodiments, the primer set that specifically amplifies SSBP2 is a forward and reverse primer having sequences selected from SEQ ID NOs:161-176, and the sequence of the probe that individually detects SSBP2 is selected from SEQ ID NOs:297 and 298. In some embodiments, the sequence of the probe that specifically detects SSBP2 is SEQ ID NO:297. In some embodiments, the primer set that specifically amplifies BCL6 is a forward and reverse primer having sequences selected from SEQ ID NOs:49-64, and the sequence of the probe that individually detects BCL6 is selected from SEQ ID NO:266-268. In some embodiments, the probe that individually detects BCL6 is SEQ ID NO:266. In some embodiments, the primer set that specifically amplifies LRMP is a forward and reverse primer having sequences selected from SEQ ID NOs:25-48, and the sequence of the probe that individually detects LRMP is selected from SEQ ID NOs:259-265. In some embodiments, the sequence of the probe that individually detects LRMP is SEQ ID NO:262. In some embodiments, the primer set that specifically amplifies ARIDA3A is a forward and reverse primer having sequences selected from SEQ ID NOs:81-96, and the sequence of the probe that individually detects ARIDA3A is selected from SEQ ID NOs:276-280. In some embodiments the sequence of the probe that individually detects ARIDA3A is SEQ ID NO:279. In some embodiments, the primer set that specifically amplifies CCND2 is a forward and reverse primer having sequences selected from SEQ ID NOs:97-112, and the sequence of the probe that individually detects CCND2 is selected from SEQ ID NOs:281-283. In some embodiments, the sequence of the probe that individually detects CCND2 is SEQ ID NO:281. In some embodiments, the primer set that specifically amplifies FOXP1 is a forward and reverse primer having sequences selected from SEQ ID NOs:221-236, and the sequence of the probe that individually detects FOXP1 is selected from SEQ ID NOs:308 and 309. In some embodiments, the sequence of the probe that individually detects FOXP1 is SEQ ID NO:309. In some embodiments, the primer set that specifically amplifies KIAA0226L is a forward and reverse primer having sequences selected from SEQ ID NOs:237-252, and the sequence of the probe that individually detects KIAA0226L is selected from SEQ ID NOs:310-314. In some embodiments, the sequence of the probe that individually detects KIAA0226L is SEQ ID NO:313. In some embodiments, the primer set that specifically amplifies JADE3 is a forward and reverse primer having sequences selected from SEQ ID NOs:145-160, and the sequence of the probe that individually detects JADE3 is selected from SEQ ID NOs:290-296. In some embodiments, the sequence of the probe that individually detects JADE3 is SEQ ID NO:292. In some embodiments, the primer set that specifically amplifies PIM2 is a forward and reverse primer having sequences selected from SEQ ID NOs:65-80, and the sequence of the probe that individually detects PIM2 is selected from SEQ ID NOs:269-275. In some embodiments, the sequence of the probe that individually detects PIM2 is SEQ ID NO:275. In some embodiments, the primer set that specifically amplifies TCF4 is a forward and reverse primer having sequences selected from SEQ ID NOs:129-144, and the sequence of the probe that individually detects TCF4 is selected from SEQ ID NOs:287-289. In some embodiments, the sequence of the probe that individually detects TCF4 is SEQ ID NO:287. In some embodiments, the primer set that specifically amplifies FAM46C is a forward and reverse primer having sequences selected from SEQ ID NOs:113-128, and the sequence of the probe that individually detects FAM46C is selected from SEQ ID NOs:284-286. In some embodiments, the sequence of the probe that individually detects FAM46C is SEQ ID NO:284.

DETAILED DESCRIPTION OF THE INVENTION

I. Introduction

Provided herein is a novel multiplex real-time, quantitative reverse transcription (qRT)-PCR classifier to determine cell-of-origin (COO) subtype of Diffuse Large B-cell Lymphoma (DLBCL). The classifier uses a qRT-PCR multiplex reaction to quantify 16 gene targets (15 determinative and 1 control) and assign a COO subtype of DLBCL. In some embodiments, the assay is a five-tube qRT-PCR. The feasibility and accuracy of the qRT-PCR classifier in formalin-fixed paraffin embedded tissues (FFPET) from DLBCL is shown herein.

The presently described assays rely on proven, widely adopted technology and provide accurate, reproducible, and rapid results.

II. Definitions

The term "multiplex" refers to an assay in which more than one target is detected.

The terms "receptacle," "vessel," "tube," "well," "chamber," "microchamber," etc. refer to a container that can hold reagents or an assay. If the receptacle is in a kit and holds reagents, or is being used for an amplification reaction, it can be closed or sealed to avoid contamination or evaporation. If the receptacle is being used for an assay, it can be open or accessible, at least during set up of the assay.

The terms "individually detected" or "individual detection," referring to a marker gene or marker gene product, indicates that each marker in a multiplex reaction is detected. That is, each marker is associated with a different label (detected by a differently labeled probe).

Unless otherwise labeled, the terms "COO classifier," "subtype classifier," "COO subtype signature," "subtype determination signature," and like terms are used to refer to the 15-gene signature that can be used to classify the cell of origin subtype of a DLBCL patient. The terms "6-gene COO classifier," "6-gene subtype classifier," "6-gene COO subtype signature," "6-gene subtype determination signature," and like terms refer to the classifier that includes CCND2, FOXP1, JADE3, ZNF318, SSBP2, and PTK2.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The term "primer" refers to a short nucleic acid (an oligonucleotide) that acts as a point of initiation of polynucleotide strand synthesis by a nucleic acid polymerase under suitable conditions. Polynucleotide synthesis and amplification reactions typically include an appropriate buffer, dNTPs and/or rNTPs, and one or more optional cofactors, and are carried out at a suitable temperature. A primer typically includes at least one target-hybridized region that is at least substantially complementary to the target sequence (e.g., having 0, 1, 2, or 3 mismatches). This region of is typically about 8 to about 40 nucleotides in length, e.g., 12-25 nucleotides. A "primer set" refers to a forward and reverse primer that are oriented in opposite directions relative to the target sequence, and that produce an amplification product in amplification conditions. The primer set can further include and additional forward or reverse primer, e.g., to carry out allele-specific amplification.

As used herein, "probe" means any molecule that is capable of selectively binding to a specifically intended target biomolecule, for example, a nucleic acid sequence of interest that hybridizes to the probes. The probe is detectably labeled with at least one non-nucleotide moiety. In some embodiments, the probe is labeled with a fluorophore and quencher.

The words "complementary" or "complementarity" refer to the ability of a nucleic acid in a polynucleotide to form a base pair with another nucleic acid in a second polynucleotide. For example, the sequence A-G-T (A-G-U for RNA) is complementary to the sequence T-C-A (U—C-A for RNA). Complementarity may be partial, in which only some of the nucleic acids match according to base pairing, or complete, where all the nucleic acids match according to base pairing. A probe or primer is considered "specific for" a target sequence if it is at least partially complementary to the target sequence. Depending on the conditions, the degree of complementarity to the target sequence is typically higher for a shorter nucleic acid such as a primer (e.g., greater than 80%, 90%, 95%, or higher) than for a longer sequence.

The term "specifically amplifies" indicates that a primer set amplifies a target sequence more than non-target sequence at a statistically significant level. The term "specifically detects" indicates that a probe will detect a target sequence more than non-target sequence at a statistically significant level. As will be understood in the art, specific amplification and detection can be determined using a negative control, e.g., a sample that includes the same nucleic acids as the test sample, but not the target sequence or a sample lacking nucleic acids. For example, primers and probes that specifically amplify and detect a target sequence result in a Ct that is readily distinguishable from background (non-target sequence), e.g., a Ct that is at least 2, 3, 4, 5, 5-10, 10-20, or 10-30 cycles less than background.

The terms "identical" or "percent identity," in the context of two or more nucleic acids, or two or more polypeptides, refer to two or more sequences or subsequences that are the same or have a specified percentage of nucleotides, or amino acids, that are the same (e.g., about 60% identity, e.g., at least any of 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters, or by manual alignment and visual inspection. See e.g., the NCBI web site at ncbi.nlm.nih.gov/BLAST. Such sequences are then said to be "substantially identical." Percent identity is typically determined over optimally aligned sequences, so that the definition applies to sequences that have deletions and/or additions, as well as those that have substitutions. The algorithms commonly used in the art account for gaps and the like. Typically, identity exists over a region comprising an a sequence that is at least about 8-25 amino acids or nucleotides in length, or over a region that is 50-100 amino acids or nucleotides in length, or over the entire length of the reference sequence.

The term "kit" refers to any manufacture (e.g., a package or a container) including at least one reagent, such as a nucleic acid probe or probe pool or the like, for specifically amplifying, capturing, tagging/converting or detecting RNA or DNA as described herein.

The term "amplification conditions" refers to conditions in a nucleic acid amplification reaction (e.g., PCR amplification) that allow for hybridization and template-dependent extension of the primers. The term "amplicon" or "amplification product" refers to a nucleic acid molecule that contains all or a fragment of the target nucleic acid sequence and that is formed as the product of in vitro amplification by any suitable amplification method. One of skill will understand that a forward and reverse primer (primer pair) defines the borders of an amplification product. The term "generate an amplification product" when applied to primers, indicates that the primers, under appropriate conditions (e.g., in the presence of a nucleotide polymerase and NTPs), will produce the defined amplification product. Various PCR conditions are described in PCR Strategies (Innis et al., 1995, Academic Press, San Diego, Calif.) at Chapter 14; *PCR Protocols: A Guide to Methods and Applications* (Innis et al., Academic Press, N Y, 1990)

The term "amplification product" refers to the product of an amplification reaction. The amplification product includes the primers used to initiate each round of polynucleotide synthesis. An "amplicon" is the sequence targeted for amplification, and the term can also be used to refer to amplification product. The 5' and 3' borders of the amplicon are defined by the forward and reverse primers.

The term "sample" or "biological sample" refers to any composition containing or presumed to contain nucleic acid. The term includes purified or separated components of cells, tissues, or blood, e.g., DNA, RNA, proteins, cell-free portions, or cell lysates. In the context of the presently disclosed assay, the sample is typically FFPET, e.g., from a tumor or metastatic lesion. The sample can also be from frozen or fresh tissue, or from a liquid sample, e.g., blood or a blood component (plasma or serum), urine, semen, saliva, sputum, mucus, semen, tear, lymph, cerebral spinal fluid, mouth/throat rinse, bronchial alveolar lavage, material washed from a swab, etc. Samples also may include constituents and components of in vitro cultures of cells obtained from an individual, including cell lines. The sample can also be partially processed from a sample directly obtained from an individual, e.g., cell lysate or blood depleted of red blood cells.

The term "obtaining a sample from an individual" means that a biological sample from the individual is provided for testing. The obtaining can be directly from the individual, or from a third party that directly obtained the sample from the individual.

A "control" sample or value refers to a value that serves as a reference, usually a known reference, for comparison to a test sample or test conditions. For example, a test sample can be taken from a test condition, e.g., from an individual suspected of having cancer, and compared to samples from known conditions, e.g., from a cancer-free individual (negative control), or from an individual known to have cancer (positive control). In the context of the present disclosure, the test sample is typically from a DLBCL patient. A control can also represent an average value or a range gathered from a number of tests or results. A control can also be prepared for reaction conditions. For example, a control for the presence, quality, and/or quantity of nucleic acid (e.g., internal control) can include primers or probes that will detect a sequence known to be present in the sample (e.g., a housekeeping gene such as beta actin, beta globin, glyceraldehyde 3-phosphate dehydrogenase (GAPDH), ribosomal protein L37 and L38, PPIase, EIF3, eukaryotic translation elongation factor 2 (eEF2), DHFR, or succinate dehydrogenase) A known added polynucleotide, e.g., having a designated length, can also be added. An example of a negative control is one free of nucleic acids, or one including primers or probes specific for a sequence that would not be present in the sample, e.g., from a different species. One of skill will understand that the selection of controls will depend on the particular assay, e.g., so that the control is cell type and organism-appropriate. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

The terms "label," "tag," "detectable moiety," and like terms refer to a composition detectable by spectroscopic, photochemical, biochemical, immunochemical, chemical, or other physical means. For example, useful labels include fluorescent dyes (fluorophores), luminescent agents, radioisotopes (e.g., $^{32}P$, $^{3}H$), electron-dense reagents, or an affinity-based moiety, e.g., a poly-A (interacts with poly-T) or poly-T tag (interacts with poly-A), a His tag (interacts with Ni), or a strepavidin tag (separable with biotin).

The term "identifying an individual" means determining based on a sample derived from an individual (e.g., a patient) whether the respective individual is actually sensitive to an administration or treatment.

The term "providing treatment for an individual" means that the treatment is actually administered to the individual (e.g., an in-patient injection), or that it is made available to the individual, so that the individual or third party actually administers the treatment.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

III. Nucleic Acid Samples

Samples for nucleic acid amplification can be obtained from any source suspected of containing nucleic acid. Samples can be taken from formalin fixed paraffin embedded tissue (FFPET), tissue biopsy, brochoalveolar lavage, or cultured cells (e.g., obtained from a patient, or representing a control). In the context of the present disclosure, the sample is typically taken from lung tissue or a cell population that includes lung cells, e.g., lung cancer cells. In some embodiments, the sample is obtained in a non-invasive manner, e.g., from urine, skin, swab, saliva, blood or a blood fraction.

In a sample that includes cells, the cells can be separated out (e.g., using size-based filtration or centrifugation), thereby leaving cell free nucleic acids (cfNA), including nucleic acids in exosomes, microvesicles, viral particles, or those circulating freely. Alternatively, the cells can be lysed to obtain cellular nucleic acids, either in the presence of magnetic glass particles (MGPs) or before addition of the cellular lysate to the MGPs.

Methods for isolating nucleic acids from biological samples are known, e.g., as described in Sambrook, and several kits are commercially available (e.g., High Pure RNA Isolation Kit, High Pure Viral Nucleic Acid Kit, and MagNA Pure LC Total Nucleic Acid Isolation Kit, DNA Isolation Kit for Cells and Tissues, DNA Isolation Kit for Mammalian Blood, High Pure FFPET DNA Isolation Kit, available from Roche). In the context of the presently disclosed methods, RNA is collected, though in some embodiments, the classifier can be used on previously prepared cDNA.

IV. Diffuse Large B Cell Lymphoma (DLBCL) and Therapies

Diffuse large B-cell lymphoma (DLBCL) is the most common subtype of non-Hodgkin lymphoma. Approximately 40% of patients have refractory disease or disease that will relapse after an initial response, and the majority of patients with relapsed DLBCL will succumb to the disease. There are two major biologically distinct molecular subtypes of DLBCL: germinal center B-cell (GCB) and activated B-cell (ABC). ABC DLBCL is associated with substantially worse outcomes when treated with standard chemotherapy.

GCB patients typically benefit from standard chemotherapy. This can include CHOP (cyclophosphamide; doxorubicin; vincristine; and prednisolone) or R-CHOP, which further includes rituximab and/or etoposide. The cocktail can be administered periodically for a set period of time, or until reduction in tumor size and/or symptoms are detected. For example, the CHOP or R-CHOP can be administered every 2 or 3 weeks. Treatment or administration typically begins with a low dose so that side effects can be determined, and the dose increased until side effects appear or within the patient's tolerance.

A number of additional agents (alternative therapies) are in development for ABC patients. These can be administered in combination with CHOP or R-CHOP, simultaneously or in separate doses. These alternative therapies can include BTK inhibitors (e.g., ibrutinib), SYK inhibitors (e.g., fostamatinib), NFkB inhibitors (e.g., bortezomib), or immunomodulatory agents (e.g., structural and functional analogs of thalidomide, e.g., lenalidomide).

Additional appropriate therapies for DLBCL GCB and ABC subtypes are described in Dunleavy et al. (Apr. 15, 2014) Oncology and Nowakowki & Czuczman (2015) *Am. Soc. Clin. Oncol. Educ. Book* e449.

V. Amplification and Detection

A nucleic acid sample can be used for detection and quantification, e.g., using nucleic acid amplification, e.g., using any primer-dependent method. In some embodiments, a preliminary reverse transcription step is carried out (also referred to as RT-PCR, not to be confused with real time PCR). See, e.g., Hierro et al. (2006) 72:7148. The term "qRT-PCR" as used herein refers to reverse transcription followed by quantitative PCR. Both reactions can be carried out in a single tube without interruption, e.g., to add reagents. For example, a polyT primer can be used to reverse transcribe all mRNAs in a sample with a polyA tail, random oligonucleotides can be used, or a primer can be designed that is specific for a particular target transcript that will be reverse transcribed into cDNA. The cDNA can form the initial template strand to be for quantitative amplification (real time or quantitative PCR, i.e., RTPCR or qPCR). qPCR allows for reliable detection and measurement of products generated during each cycle of PCR process. Such techniques are well known in the art, and kits and reagents are commercially available, e.g., from Roche Molecular Systems, Life Technologies, Bio-Rad, etc. See, e.g., Pfaffl (2010) *Methods: The ongoing evolution of qPCR* vol. 50.

A separate reverse transcriptase and thermostable DNA polymerase can be used, e.g., in a two-step (reverse transcription followed by addition of DNA polymerase and amplification) or combined reaction (with both enzymes added at once). In some embodiments, the target nucleic acid is amplified with a thermostable polymerase with both reverse transcriptase activity and DNA template-dependent activity. Exemplary enzymes include Tth DNA polymerase, the C. therm Polymerase system, and those disclosed in US20140170730 and US20140051126.

Probes for use as described herein can be labeled with a fluorophore and quencher (e.g., TaqMan, LightCycler, Molecular Beacon, Scorpion, or Dual Labeled probes). Appropriate fluorophores include FAM, JOE, TET, Cal Fluor Gold 540, HEX, VIC, Cal Fluor Orang 560, TAMRA, Cyanine 3, Quasar 570, Cal Fluor Red 590, Rox, Texas Red, Cyanine 5, Quasar 670, and Cyanine 5.5. Appropriate quenchers include TAMRA (for FAM, JOE, and TET), DABCYL, and BHQ1-3.

Detection devices are known in the art and can be selected as appropriate for the selected labels. Detection devices appropriate for quantitative PCR include the Cobas® and Light Cycler® systems (Roche), PRISM 7000 and 7300 real-time PCR systems (Applied Biosystems), etc. Six-channel detection is available on the CFX96 Real Time PCR Detection System (Bio-Rad) and Rotorgene Q (Qiagen), allowing for a higher degree of multiplexing.

Results can be expressed in terms of a threshold cycle (abbreviated as Ct, and in some instances Cq or Cp). A lower Ct value reflects the rapid achievement of a predetermined threshold level, e.g., because of higher target nucleic acid concentration or a more efficient amplification. A higher Ct value may reflect lower target nucleic acid concentration, or inefficient or inhibited amplification. The threshold cycle is generally selected to be in the linear range of amplification for a given target. In some embodiments, the Ct is set as the cycle at which the growth signal exceeds a pre-defined threshold line, e.g., in relation to the baseline, or by determining the maximum of the second derivation of the growth curve. Determination of Ct is known in the art, and described, e.g., in U.S. Pat. No. 7,363,168.

VI. Kits

Provided herein are kits for multiplex qRT-PCR assays to classify the COO subtype of a DLBCL patient. In some embodiments, the kit includes mixtures of primers and probes for amplification, detection, and quantification of GCB and ABC marker gene products (RNA). GCB markers include ZNF318, PDK3, HMGN1, PTK2, SSBP2, BCL6, and LRMP, and transcripts of these genes are present at a higher level in samples from GCB patients than in samples from non-cancer or ABC patients. ABC markers include ARID3A, CCND2, FOXP1, KIAA0226L, JADE3, PIM2, TCF4, and FAM46C, and transcripts of these genes are present at a higher level in samples from ABC patients than in samples from non-cancer or GCB patients.

Kits for multiplex qRT-PCR assays to classify the 6-gene COO subtype of a DLBCL patient are also included herein. In some embodiments, the kit includes mixtures of primers and probes for amplification, detection, and quantification of GCB and ABC marker gene products (RNA). GCB markers include ZNF318, PTK2, and SSBP2, and transcripts of these genes are present at a higher level in samples from GCB patients than in samples from non-cancer or ABC patients. ABC markers include CCND2, FOXP1, and JADE3, transcripts of these genes are present at a higher level in samples from ABC patients than in samples from non-cancer or GCB patients.

The marker-specific primer sets and probes can be mixed and matched in any combination. For example, each marker can be individually detected. In a detection system having 6 channels, up to 5 markers can be detected in a single vessel, along with the internal control. In this case, only 3 primer set and probe mixtures are required to include all 15 markers. In a detection system having 4 channels, up to 3 markers can be detected in a single vessel, along with the internal control. In this case, 5 primer set and probe mixtures are required. Alternatively, the assay can be carried out with a lower degree of multiplexing, or in non-multiplex fashion, so that more primer set and probe mixtures are required to test expression of all 15 markers in a sample. An example of a 5-tube multiplex assay is shown in the Examples. Thus in some embodiments, the kit includes 5 mixtures (e.g., master mixes), each comprising a primer set and probe specific for up to three GCB and ABC probe markers, and a primer set and probe specific for an internal control gene.

For the 6-gene COO signature, the kit can include 2 mixtures, e.g., (i) a mixture including primers and probes that specifically amplify and detect GCB markers include ZNF318, PTK2, and SSBP2 (and an internal control) and (ii) a mixture including primers and probes that specifically amplify and detect ABC markers include CCND2, FOXP1, and JADE3 (and an internal control). In some embodiments, the probe for each gene in mixture (i) and (ii) has a different label so that the expression of each gene can be individually detected. In some embodiments, the probe for each of the determinative gene (not an internal control) in mixture (i) and (ii) has the same label. In some embodiments, the kit includes 6 different mixtures, one for each gene in the 6-gene COO signature.

In some embodiments, markers are not detected individually. For example, all of the probes specific for GCB markers can be labeled with the same label, and all of the probes specific for ABC markers can be labeled with the same label (different from that on the GCB probes). In this case, all 15 markers can be massively multiplexed in a single vessel for detection with only 3 channels (one for GCB marker probes, one for ABC marker probes, and one for the control probe).

In some embodiments, the mixtures further comprise buffers, dNTPs, and other elements (e.g., cofactors or aptamers) appropriate for reverse transcription and amplification. Typically, the mixture is concentrated, so that an aliquot is added to the final reaction volume, along with sample (e.g., RNA), enzymes, and/or water. In some embodiments, the kit further comprises reverse transcriptase (or an enzyme with reverse transcriptase activity), and/or DNA polymerase (e.g., thermostable DNA polymerase such as Taq, ZO5, and derivatives thereof).

In some embodiments, the kit further includes components for RNA purification from a sample, e.g., an FFPET sample. For example, the kit can include components from High Pure or MagNA Pure FFPE RNA Isolation Kits (Roche), RNeasy FFPE Kit (Qiagen), PureLink FFPE RNA Isolation Kit (Thermo Fisher), etc.

In some embodiments, the kit further includes at least one control sample, e.g., nucleic acids from non-cancer sample (or pooled samples), or from a known ABC or GCB sample (or pooled samples). In some embodiments, the kit includes an ABC positive control and/or a GCB positive control. In some embodiments, the kit includes a negative control, e.g., lacking nucleic acids, or lacking ABC and/or GCB marker nucleic acids. In some embodiments, the kit further includes consumables, e.g., plates or tubes for nucleic acid preparation, tubes for sample collection, etc. In some embodiments, the kit further includes instructions for use, reference to a website, or software.

VII. Examples

Design of COO Subtype Determination Signature

A set of commercially acquired DLBCL FFPET specimens (Training cohort 1; n=32) was used to select the classifier genes (Table 1). The samples were prepared using the FFPET RNA kit from Roche.

Gene targets in the qRT-PCR classifier were derived from a collection of genes (n=76) screened in a cohort of DLBCL specimens (n=32; Training cohort). We used the Affymetrix microarray platform as a "gold standard" for confirmation.

TABLE 1 qRT-PCR COO classifier for DLBCL with GenBank Accession Numbers

| GCB genes | ABC genes | Control (reference) gene |
|---|---|---|
| ZNF318 | ARIDA3A | Internal control (IC) |
| Zinc finger protein 318 | AT-rich interaction domain 3A | |
| CH471081.1 (GeneID 24149) | CH471139.2 (GeneID 1820) | |
| PDK3 | CCND2 | |
| Pyruvate dehydrogenase kinase 3 | Cyclin D2 | |
| C471074 (GeneID 5165) | CH471116.2 (GeneID 894) | |
| HMGN1 | FOXP1 | |
| High mobility group nucleosome binding domain 1 | Forkhead box P1 | |
| CH471079.2 (GeneID 3150) | CH471055.1 (GeneID 27086) | |
| PTK2 | KIAA0226L | |
| Protein tyrosine kinase 2 | KIAA0226 like | |
| CH471060.1 (GeneID 5747) | CH471075.1 (GeneID 80183) | |
| SSBP2 | JADE3 | |
| Single stranded DNA binding protein 2 | Jade family PHD finger 3 | |
| CH471084.1 (GeneID 23635) | CH471164.1 (GeneID 9767) | |
| BCL6 | PIM2 | |
| B cell CLL/lymphoma 6 | Pim2 serine/threonine kinase | |
| CH471052.2 (GeneID 604) | CH471224.1 (GeneID 11040) | |
| LRMP | TCF4 | |

TABLE 1-continued qRT-PCR COO classifier for DLBCL with GenBank Accession Numbers

| GCB genes | ABC genes | Control (reference) gene |
|---|---|---|
| Lymphoid restricted membrane protein CH471094.1 (GeneID 4033) | Transcription factor 4 CH471096.1 (GeneID 6925) FAM46C Family with sequence similarity 46 member C CH471122.1 (GeneID 54855) | |

Once the genes were selected, a qRT-PCR assay was designed to be performed in 5 separate wells. 200 ng RNA test and control sample (40 ng/well) was used.

Reaction conditions were as follows for each reaction:
25 ul RNA+25 ul reaction mix
Reaction mix: 5 ul manganese acetate+10 ul RNA master mix stock+10 ul primer/probe mix (final concentration 100-300 nM)

Reactions were run in a Cobas® LC480 with four filters to detect probes as indicated in Table 2.

TABLE 2

Exemplary assay lay-out

| Label | Well 1 | Well 2 | Well 3 | Well 4 | Well 5 |
|---|---|---|---|---|---|
| FAM | ARID3A | TCF4 | PDK3 | SSBP2 | JADE3 |
| HEX | CCND2 | ZNF318 | HMGN1 | BCL6 | PIM2 |
| JA270 | FOXP1 | KIAA0226L | PTK2 | LRMP | FAM46C |
| CY5.5 | IC | IC | IC | IC | IC |

Table 2 shows an exemplary assay design, and allows individual detection and quantification of each of the marker genes in a minimal number of wells.

More or fewer reaction vessels can be used. For example, a one-tube assay having all of the GCB markers labeled with the same label (fluorophore 1), all of the ABC markers labeled with the same label (fluorophore 2), and an internal control (IC) labeled with a different label (fluorophore 3) can be used. On the other end of the spectrum, each classifier gene can be detected in a separate well to determine the COO subtype of the test sample. The test is carried out by comparing the expression level of the GCB markers to the expression level of the ABC markers within a sample. If the ratio of GCB marker expression to ABC marker expression is higher than a threshold (e.g., GCB threshold), the result indicates that the sample is from an individual with GCB DLBCL. If the ratio of ABC marker expression to GCB marker expression is higher than a threshold (e.g., ABC threshold), the result indicates that the sample is from an individual with ABC DLBCL. The internal control is used to standardize expression levels based on the amount or quality of nucleic acid in the sample.

The threshold levels are based on the probability that the GCB and ABC expression levels in a sample from an individual accurately classify the individual's DLBCL COO subtype. For example, a GCB threshold level can be set using a sample from an individual (or group of individuals) known to have GCB subtype. A GCB positive control can then be prepared with the known GCB sample. In some embodiments, the GCB positive control is prepared from the known GCB sample mixed with a sample known to be from an individual with ABC so that >50% of the nucleic acids in the GCB positive control are from the known GCB sample to provide a minimum GCB:ABC expression level ratio. If a sample has a GCB:ABC expression ratio above that ratio (GCB threshold), the result is considered an accurate call of GCB COO subtype. The GCB positive control can be prepared with 51-100% known GCB sample, e.g., about 55, 58, 60, 62, 65, 68, 70, 75% or higher, with higher percentages resulting in a more stringent confidence level in the GCB threshold. If a sample has a GCB:ABC expression ratio below the GCB threshold, the result is either not determined, or an ABC COO subtype. The ABC threshold is set similarly. For example, the ABC positive control can be prepared with 51-100% known ABC sample, e.g., about 55, 58, 60, 62, 65, 68, 70, 75% or higher, with higher percentages resulting in a more stringent confidence level in the ABC threshold. If a sample has an ABC:GCB expression ratio above the ABC threshold, the result is considered an accurate call of ABC COO subtype, while a ratio below the ABC threshold, the result is not determined, or a GCB COO subtype. In some embodiments, the GCB and ABC positive controls are prepared by mixing a known amount of GCB marker nucleic acids and ABC marker nucleic acids. The GCB and ABC positive controls also act as controls for assay performance, e.g., to ensure reagents are added and that the instrument is performing properly.

Tables 3 and 4 show the sequences of primers and probes, respectively, that can be used for the present classifier.

TABLE 3

Primer sequences

| Gene | Forward primer | 5' to 3' Sequence (SEQ ID NO) | Reverse Primer | 5' to 3' Sequence (SEQ ID NO) |
|---|---|---|---|---|
| PTK2 | CS_PTK2_F1 | GGCAGTATTGACAGGGAGGA (1) | CS_PTK2_R1 | TGGTTTACCCACAGGCTGA (2) |
| PTK2 | CS_PTK2_F2 | GGAGAAGGCCAATTTGGAGAT (3) | CS_PTK2_R2 | ACAGTTTTTACATGTTTTAATTGCAACC (4) |
| PTK2 | CS_PTK2_F3 | GGACAGAAAAGGAATGCTACAACTA (5) | CS_PTK2_R3 | CGCAATGGTTAGGGATGGTG (6) |

TABLE 3 -continued

Primer sequences

| Gene | Forward primer | 5' to 3' Sequence (SEQ ID NO) | Reverse Primer | 5' to 3' Sequence (SEQ ID NO) |
|---|---|---|---|---|
| PTK2 | CS_PTK2_F4 | AGCTTAGTACAGCTCTTGCAT (7) | CS_PTK2_R4 | TCATTTGAGGACACCAGAACATT (8) |
| PTK2 | CS_PTK2_F5 | GCCCAGAAGAAGGAATCAGTT (9) | CS_PTK2_R5 | GGTTTGCACTTGAGTGAAGTC (10) |
| PTK2 | CS_PTK2_F6 | ACCATTCCCCTCCTACCAG (11) | CS_PTK2_R6 | CTCACCCAGGTCAGAGTTCA (12) |
| PTK2 | CS_PTK2_F7 | GACCTCAGGAGATAGCAATGT (13) | CS_PTK2_R7 | CACTTGCCCAATCCCTCG (14) |
| PTK2 | CS_PTK2_F8 | GAATGGAACCTCGCAGTCAT (15) | CS_PTK2_R8 | GGCCAACTTTGGTATTGATGG (16) |
| PTK2 | CS_PTK2_F9 | TTCGACGTTTTACCTCAGCT (17) | CS_PTK2_R9 | GGCTTCACACCATGCATCAG (18) |
| PTK2 | CS_PTK2_F10 | GAAAGAAGGTGAACGGGCTT (19) | CS_PTK2_R10 | GTGTGTCCGCATGCCTTG (20) |
| PTK2 | CS_PTK2_F11 | CCTGTCTGGATAATCATGGAGC (21) | CS_PTK2_R11 | GCTAGATCCAAACTGTATTTCCTTAC (22) |
| PTK2 | CS_PTK2_F12 | CGGCCCAGGTTTACTGAAC (23) | CS_PTK2_R12 | TCTTCTTGCTGAGCCTTCTCT (24) |
| LRMP | LRMP_F1 | CAGGCTGCATCAGGATGAAT (25) | LRMP_R1 | CAGCAGGCTCTCAGGACA (26) |
| LRMP | LRMP_F2 | CTCTCAGGCTGCATCAGGA (27) | LRMP_R1 | CAGCAGGCTCTCAGGACA (28) |
| LRMP | LRMP_F3 | ACAAGATCAGCTTCTCCCAC (29) | LRMP_R2 | CTCGTAGAGTCTTGGAATGCA (30) |
| LRMP | LRMP_F4 | CAAGATCAGCTTCTCCCACG (31) | LRMP_R3 | CTCGTAGAGTCTTGGAATGCAAT (32) |
| LRMP | LRMP_F5 | AGGAACCAGAAACAATAGAAGAACA (33) | LRMP_R4 | CGATTTCACAGTGGTTACAGGA (34) |
| LRMP | LRMP_F6 | GCCAAAGAGGAACCAGAAACA (35) | LRMP_R5 | ACCGATTTCACAGTGGTTACA (36) |
| LRMP | LRMP_F7 | CAGTAGGGCTGAGATGTTGG (37) | LRMP_R6 | ACGTGCTGAATCATCACTTCAA (38) |
| LRMP | LRMP_F8 | GGCCAGTAGGGCTGAGAT (39) | LRMP_R6 | ACGTGCTGAATCATCACTTCAA (40) |
| LRMP | LRMP_F9 | GACTGCCAAATTAAAAAACGTTCA (41) | LRMP_R7 | TTTCTGGGTAAAGAGGCAATAGTC (42) |
| LRMP | LRMP_F10 | GGAAGCCAAGTCTTTCTGAAAAG (43) | LRMP_R8 | GAGGACTTGAGATTGTTGCC (44) |
| LRMP | LRMP_F11 | GGCAGAAGAAAATTTGAAGAAAGAAA (45) | LRMP_R9 | AATGATTTCCTGTGCCTGGT (46) |
| LRMP | LRMP_F12 | GGTGGCTGGGATGGAAAATAA (47) | LRMP_R10 | GGACGGTGTTCACTCTGCT (48) |
| BCL6 | BCL6_F1 | GAAGAGCCACCTGCGAATC (49) | BCL6_R1 | GCTGGCTTTTGTGACGGAAA (50) |
| BCL6 | BCL6_F2 | CCACCTGCGAATCCACAC (51) | BCL6_R2 | CTGGCTTTTGTGACGGAAATG (52) |
| BCL6 | BCL6_F1 | GAAGAGCCACCTGCGAATC (53) | BCL6_R3 | GCTGGCTTTTGTGACGGAA (54) |
| BCL6 | BCL6_F2 | CCACCTGCGAATCCACAC (55) | BCL6_R1 | GCTGGCTTTTGTGACGGAAA (56) |

TABLE 3 -continued

Primer sequences

| Gene | Forward primer | 5' to 3' Sequence (SEQ ID NO) | Reverse Primer | 5' to 3' Sequence (SEQ ID NO) |
|---|---|---|---|---|
| BCL6 | BCL6_F3 | CATGTTGTGGACACTTGCC (57) | BCL6_R4 | CTTCACGAGGAGGCTTGATG (58) |
| BCL6 | BCL6_F4 | GGAGCATGTTGTGGACACTT (59) | BCL6_R5 | CTCTTCACGAGGAGGCTTGA (60) |
| BCL6 | BCL6_F5 | ATGGAGCATGTTGTGGACAC (61) | BCL6_R6 | CGAGGAGGCTTGATGGCA (62) |
| BCL6 | BCL6_F6 | GGACTCCACCATCCCACAA (63) | BCL6_R7 | TAGAGTGGTGAGTGGCTCTC (64) |
| PIM2 | PIM2_FP1 | GTGCCCTGCTTCATGATG (65) | PIM2_RP1 | CTGGTGTCGAGAGATCCACTC (66) |
| PIM2 | PIM2_FP2 | GGCTGTGCCAAACTCATT (67) | PIM2_RP2 | GGGCTGTACACCCTTGT (68) |
| PIM2 | PIM2_FP1 | GTGCCCTGCTTCATGATG (69) | PIM2_RP3 | CATGGTACTGGTGTCGAGAGA (70) |
| PIM2 | PIM2_FP1 | GTGCCCTGCTTCATGATG (71) | PIM2_RP4 | CCGGGAGTGCATGGTACT (72) |
| PIM2 | PIM2_FP3 | GGACACCGCCTCACAGAT (73) | PIM2_RP5 | AGTGGGCATGTGACTGAGTC (74) |
| PIM2 | PIM2_FP3 | GGACACCGCCTCACAGAT (75) | PIM2_RP6 | CTTCGAGTGGGCATGTGA (76) |
| PIM2 | PIM2_FP4 | CGCCTCACAGATCGACTC (77) | PIM2_RP7 | GCAGTGCGACTTCGAGTG (78) |
| PIM2 | PIM2_FP5 | ACCGTCTTCGCAGGACAC (79) | PIM2_RP8 | GGGCATGTGACTGAGTCTG (80) |
| ARID3A | ARID3A_FP1 | GGCGACTGGACTTACGAGG (81) | ARID3A_RP1 | CCAGGAATTCCTTCCTCTTGG (82) |
| ARID3A | ARID3A_FP2 | TCCTGGATGACTTGTTCAGC (83) | ARID3A_RP2 | AGGACCTGTTTGGCCATGAT (84) |
| ARID3A | ARID3A_FP3 | ACGTCCATCACCAGTGCA (85) | ARID3A_RP3 | CTTCTCACACTCGTAGGGGT (86) |
| ARID3A | ARID3A_FP3 | ACGTCCATCACCAGTGCA (87) | ARID3A_RP4 | CCCGCTTCTCACACTCGTA (88) |
| ARID3A | ARID3A_FP4 | CAGCTGCCCATGAGCATTC (89) | ARID3A_RP5 | TCAGGTTCACAGCAGAGTCC (90) |
| ARID3A | ARID3A_FP4 | CAGCTGCCCATGAGCATTC (91) | ARID3A_RP6 | CGTCAGGTTCACAGCAGAG (92) |
| ARID3A | ARID3A_FP5 | AGCATGTCGGTGGAGATCAA (93) | ARID3A_RP7 | TTGGGAGCAGAGGTTGGC (94) |
| ARID3A | ARID3A_FP6 | ATCAGCATGTCGGTGGAGAT (95) | ARID3A_RP8 | TTTGTTGGGAGCAGAGGTTG (96) |
| CCND2 | CCND2_FP1 | AGGACATCCAACCCTACATGC (97) | CCND2_RP1 | GAAGACCTCTTCTTCGCACT (98) |
| CCND2 | CCND2_FP2 | CTTCATTGCTCTGTGTGCCA (99) | CCND2_RP2 | TGCTCCCACACTTCCAGTT (100) |
| CCND2 | CCND2_FP2 | CTTCATTGCTCTGTGTGCCA (101) | CCND2_RP3 | CCACACTTCCAGTTGCGATC (102) |
| CCND2 | CCND2_FP3 | GACTGAGCTGCTGGCTAAGA (103) | CCND2_RP4 | GAGCACCGCCTCAATCTG (104) |
| CCND2 | CCND2_FP4 | GGACATCCAACCCTACATGC (105) | CCND2_RP5 | AGAGGGAAGACCTCTTCTTCG (106) |

TABLE 3 -continued

Primer sequences

| Gene | Forward primer | 5' to 3' Sequence (SEQ ID NO) | Reverse Primer | 5' to 3' Sequence (SEQ ID NO) |
|---|---|---|---|---|
| CCND2 | CCND2_FP4 | GGACATCCAACCCTACATGC (107) | CCND2_RP6 | GGAAGACCTCTTCTTCGCACT (108) |
| CCND2 | CCND2_FP2 | CTTCATTGCTCTGTGTGCCA (109) | CCND2_RP7 | CTGCTCCCACACTTCCAGT (110) |
| CCND2 | CCND2_FP5 | ACCTTCATTGCTCTGTGTGC (111) | CCND2_RP8 | GCTCCCACACTTCCAGTTG (112) |
| FAM46C | FAM46C_FP1 | AAGGACCTGCCTCTGTCG (113) | FAM46C_RP1 | TCTCCTCTGCCATCTTCAGG (114) |
| FAM46C | FAM46C_FP2 | CCAAGGACCTGCCTCTGT (115) | FAM46C_RP2 | CTCCTCTGCCATCTTCAGGG (116) |
| FAM46C | FAM46C_FP3 | CCAAGGACCTGCCTCTGTC (117) | FAM46C_RP1 | TCTCCTCTGCCATCTTCAGG (118) |
| FAM46C | FAM46C_FP4 | CCAAGGACCTGCCTCTGTC (119) | FAM46C_RP2 | CTCCTCTGCCATCTTCAGGG (120) |
| FAM46C | FAM46C_FP5 | CAAGGACCTGCCTCTGTCG (121) | FAM46C_RP1 | TCTCCTCTGCCATCTTCAGG (122) |
| FAM46C | FAM46C_FP2 | CCAAGGACCTGCCTCTGT (123) | FAM46C_RP3 | CTCTGCCATCTTCAGGGGAT (124) |
| FAM46C | FAM46C_FP1 | AAGGACCTGCCTCTGTCG (125) | FAM46C_RP4 | TGCTCTCCTCTGCCATCTTC (126) |
| FAM46C | FAM46C_FP3 | CCAAGGACCTGCCTCTGTC (127) | FAM46C_RP5 | CTCTGCCATCTTCAGGGGAT (128) |
| TCF4 | TCF4_FP1 | AAACCAGCAACCAGCACTTT (129) | TCF4_RP1 | GAGGAGCTCCAAGGGTCAC (130) |
| TCF4 | TCF4_FP2 | CAACCAGCACTTTCCCTAGC (131) | TCF4_RP2 | CCACTGGAGGAGCTCCAAG (132) |
| TCF4 | TCF4_FP3 | ACTTCCCCTGACCTGAACC (133) | TCF4_RP3 | GAGACACTCTGCCCCTGTAG (134) |
| TCF4 | TCF4_FP4 | CGACTTCCCCTGACCTGAA (135) | TCF4_RP4 | GAGACACTCTGCCCCTGTAG (136) |
| TCF4 | TCF4_FP5 | GCAACCAGCACTTTCCCTAG (137) | TCF4_RP5 | ATTCATCCCACTGGAGGAGC (138) |
| TCF4 | TCF4_FP6 | TGGCCGTCATCCTCAGTC (139) | TCF4_RP6 | CCTCCCTTCTTTTCAGACACG (140) |
| TCF4 | TCF4_FP7 | GTGGCCGTCATCCTCAGTC (141) | TCF4_RP7 | TCTTTTCAGACACGCAGCTT (142) |
| TCF4 | TCF4_FP8 | GTGGCCGTCATCCTCAGT (143) | TCF4_RP7 | TCTTTTCAGACACGCAGCTT (144) |
| JADE3 | JADE3_FP1 | TCAAGTCAAAAATTCCAAATGAACAC (145) | JADE3_RP1 | TGGAAGTTTCATGGCACTGA (146) |
| JADE3 | JADE3_FP2 | TACCAGCCAGTCCAGACAC (147) | JADE3_RP2 | TCGGATAAACAGAACGTCCTT (148) |
| JADE3 | JADE3_FP3 | GGCTTCAGGAACTCAATGAAGA (149) | JADE3_RP3 | CAGGACTTCTACTGTCTTTTCCA (150) |
| JADE3 | JADE3_FP3 | GGCTTCAGGAACTCAATGAAGA (151) | JADE3_RP4 | GGCGTTCCAGGACTTCTACT (152) |
| JADE3 | JADE3_FP4 | GGGAATGATATGGTGTTCTGTGA (153) | JADE3_RP5 | CCTTCTGGGACCTTGAGGA (154) |
| JADE3 | JADE3_FP5 | ACTAAATGGGCTCATGTCAGC (155) | JADE3_RP6 | ATCGGTTCCATCCTCTCAGG (156) |

TABLE 3 -continued

Primer sequences

| Gene | Forward primer | 5' to 3' Sequence (SEQ ID NO) | Reverse Primer | 5' to 3' Sequence (SEQ ID NO) |
|---|---|---|---|---|
| JADE3 | JADE3_FP6 | TGAGAATGTTTATGCATCTACGC (157) | JADE3_RP7 | AGCTTCTCTCGTCTGCTTATC A (158) |
| JADE3 | JADE3_FP7 | GGTTTGCAAGTCCAGCTTCT (159) | JADE3_RP8 | TGGTGGGTAAAACAGTGAGT TT (160) |
| SSBP2 | SSBP2_F1 | GCCACCAGGAACACCCAT (161) | SSBP2_R1 | GGTCCAGGAGGTACTGCATT (162) |
| SSBP2 | SSBP2_F2 | ACATGTATACTTTAATGAATGC AGTACC (163) | SSBP2_R2 | TGGGACCATCTGACCCAG (164) |
| SSBP2 | SSBP2_F3 | AACATGTATACTTTAATGAATG CAGTACC (165) | SSBP2_R3 | ATGGGACCATCTGACCCAG (166) |
| SSBP2 | SSBP2_F1 | GCCACCAGGAACACCCAT (167) | SSBP2_R4 | CCAGGAGGTACTGCATTCAT T (168) |
| SSBP2 | SSBP2_F1 | GCCACCAGGAACACCCAT (169) | SSBP2_R5 | GTCCAGGAGGTACTGCATTC A (170) |
| SSBP2 | SSBP2_F2 | ACATGTATACTTTAATGAATGC AGTACC (171) | SSBP2_R3 | ATGGGACCATCTGACCCAG (172) |
| SSBP2 | SSBP2_F1 | GCCACCAGGAACACCCAT (173) | SSBP2_R7 | TCCAGGAGGTACTGCATTCA TT (174) |
| SSBP2 | SSBP2_F1 | GCCACCAGGAACACCCAT (175) | SSBP2_R8 | TAGGTCCAGGAGGTACTGCA (176) |
| PDK3 | PDK3_F1 | AACAGTATTACCTGGTAGCTCC (177) | PDK3_R1 | AGGGCACATAAACCACCTGA (178) |
| PDK3 | PDK3_F2 | ATCGATCCCACCTGTAACGT (179) | PDK3_R2 | CAGGTAATACTGTTCACACA GCA (180) |
| PDK3 | PDK3_F3 | GAACAGTATTACCTGGTAGCTCC (181) | PDK3_R3 | GAGGGCACATAAACCACCTG (182) |
| PDK3 | PDK3_F2 | ATCGATCCCACCTGTAACGT (183) | PDK3_R4 | CCAGGTAATACTGTTCACAC AGC (184) |
| PDK3 | PDK3_F3 | GAACAGTATTACCTGGTAGCTCC (185) | PDK3_R5 | GGGCACATAAACCACCTGAA (186) |
| PDK3 | PDK3_F1 | AACAGTATTACCTGGTAGCTCC (187) | PDK3_R6 | GTGAGGGCACATAAACCACC (188) |
| PDK3 | PDK3_F2 | ATCGATCCCACCTGTAACGT (189) | PDK3_R7 | CAGGTAATACTGTTCACACA GC (190) |
| PDK3 | PDK3_F4 | TCGCCGCTCTCCATCAAA (191) | PDK3_R8 | GCACAGGAAGTTCCTTTCGT A (192) |
| ZNF318 | ZNF318_FP1 | GAAGATCTCTGATGAGAAGA ACCG (193) | ZNF318_RP1 | GCTTCCCGGTCATTCTTTAGT T (194) |
| ZNF318 | ZNF318_FP2 | TGCCATAAAGCGCACTGAC (195) | ZNF318_RP2 | GGCAATAAAATCCACTGATG GGA (196) |
| ZNF318 | ZNF318_FP3 | GTACTATCTTAGGACCGAGTT AGAG (197) | ZNF318_RP3 | GCCATCCTTCTCCCTTCGTT (198) |
| ZNF318 | ZNF318_FP4 | ATGCCATAAAGCGCACTGAC (199) | ZNF318_RP4 | GGCAATAAAATCCACTGATG GG (200) |
| ZNF318 | ZNF318_FP5 | TGTACTATCTTAGGACCGAGT TAGAG (201) | ZNF318_RP5 | GCCATCCTTCTCCCTTCGTT (202) |
| ZNF318 | ZNF318_FP6 | AGATGTACTATCTTAGGACCG AGT (203) | ZNF318_RP6 | CCATCCTTCTCCCTTCGTTT (204) |
| ZNF318 | ZNF318_FP7 | GCCATAAAGCGCACTGACAA (205) | ZNF318_RP4 | GGCAATAAAATCCACTGATG GG (206) |

TABLE 3 -continued

Primer sequences

| Gene | Forward primer | 5' to 3' Sequence (SEQ ID NO) | Reverse Primer | 5' to 3' Sequence (SEQ ID NO) |
|---|---|---|---|---|
| ZNF318 | ZNF318_FP8 | GTACTATCTTAGGACCGAGTTAGAG (207) | ZNF318_RP7 | CCATCCTTCTCCCTTCGTTTC (208) |
| HMGN1 | HMGN1_FP1 | AAGACTTACCTGCGGAAAACG (209) | HMGN1_RP1 | TGGCTTCTTTCTCTCCTGCT (210) |
| HMGN1 | HMGN1_FP2 | AGACTTACCTGCGGAAAACG (211) | HMGN1_RP2 | TTGGCTTCTTTCTCTCCTGC (212) |
| HMGN1 | HMGN1_FP1 | AAGACTTACCTGCGGAAAACG (213) | HMGN1_RP3 | CTTGGCTTCTTTCTCTCCTGC (214) |
| HMGN1 | HMGN1_FP3 | GACTTACCTGCGGAAAACGG (215) | HMGN1_RP2 | TTGGCTTCTTTCTCTCCTGC (216) |
| HMGN1 | HMGN1_FP2 | AGACTTACCTGCGGAAAACG (217) | HMGN1_RP1 | TGGCTTCTTTCTCTCCTGCT (218) |
| HMGN1 | HMGN1_FP1 | AAGACTTACCTGCGGAAAACG (219) | HMGN1_RP2 | TTGGCTTCTTTCTCTCCTGC (220) |
| FOXP1 | FOXP1FP1 | CAACGAGAGTGACAGCAGTC (221) | FOXP1_RP1 | GGCTCTTCTTTGACGTGTACA (222) |
| FOXP1 | FOXP1_FP1 | CAACGAGAGTGACAGCAGTC (223) | FOXP1_RP2 | GGGCTCTTCTTTGACGTGTA (224) |
| FOXP1 | FOXP1_FP2 | CGCCTACTGCACACCTCTC (225) | FOXP1_RP3 | CATGGAAGCGGTAGTGTATAGAG (226) |
| FOXP1 | FOXP1_FP2 | CGCCTACTGCACACCTCTC (227) | FOXP1_RP4 | CCATGGAAGCGGTAGTGTATAG (228) |
| FOXP1 | FOXP1_FP2 | CGCCTACTGCACACCTCTC (229) | FOXP1_RP5 | CCATGGAAGCGGTAGTGTA (230) |
| FOXP1 | FOXP1_FP3 | AGAGCAGCCACGCCTACT (231) | FOXP1_RP3 | CATGGAAGCGGTAGTGTATAGAG (232) |
| FOXP1 | FOXP1_FP4 | CGAAGGCCACAAAAGATCA (233) | FOXP1_RP6 | GCATTGAGAGGTGTGCAGTA (234) |
| FOXP1 | FOXP1_FP5 | ATGGACAGTGGATGAAGTAGAATTC (235) | FOXP1_RP7 | GCTGCTCTGCATGTTTTTAATAA (236) |
| KIAA0226L | KIAA0226L_F1 | TCTTCCCATTTCAGACAGCA (237) | KIAA0226L_R1 | GAGGACTGGAAGCACTGTTT (238) |
| KIAA0226L | KIAA0226L_F1 | TCTTCCCATTTCAGACAGCA (239) | KIAA0226L_R2 | GGAGGACTGGAAGCACTGT (240) |
| KIAA0226L | KIAA0226L_F2 | AGCAAGAGTCTGGGTCTTCTA (241) | KIAA0226L_R3 | GTTTCAGTCACTGGGCTGAC (242) |
| KIAA0226L | KIAA0226L_F3 | AGCAAGAGTCTGGGTCTTCT (243) | KIAA0226L_R4 | TTTCAGTCACTGGGCTGAC (244) |
| KIAA0226L | KIAA0226L_F4 | ACAGAAACCTGTAGCTGTTCC (245) | KIAA0226L_R5 | GCTCTTTGGCTAATAGTTCTGCA (246) |
| KIAA0226L | KIAA0226L_F4 | ACAGAAACCTGTAGCTGTTCC (247) | KIAA0226L_R6 | GCTCTTTGGCTAATAGTTCTGC (248) |
| KIAA0226L | KIAA0226L_F5 | AATTCTCAGCTGGCAGGTTC (249) | KIAA0226L_R7 | GATTCAAAGTCTTTTCGGACACA (250) |
| KIAA0226L | KIAA0226L_F6 | TGGGCTCCTCCTAGATTTCA (251) | KIAA0226L_R8 | AGAAAAAATTCTGGGCTGCCA (252) |

TABLE 4

Probe sequences

| Gene | Probe_label | 5' to 3' Sequence (SEQ ID NO) |
|---|---|---|
| PTK2 | CS_PTK2_JA270_5B | CAAGGGCTGCAATCCCACACATCTTGC (253) |
|  | CS_PTK2_JA270_1C | AAGTCTTCAGGGTCCGATTGGAAACCAACA (254) |
|  | CS_PTK2_JA270_2C | AGGCATTTATATGAGTCCAGAGAATCCAGCTTTGG (255) |
|  | CS_PTK2_JA270_4B | AGGTGCACCCGAGCCTCTGACAG (256) |
|  | CS_PTK2_JA270_3A | CAAAAGATTTGTACACAGGGACATTGCTGCTCG (257) |
|  | CS_PTK2_JA270_7 | TAACGGACAAGGGCTGCAATCCCACAC (258) |
| LRMP | LRMP_JA270_1 | TGACCCAAGTATGGAAGAGAATGGTGTTGAACG (259) |
|  | LRMP_JA270_2 | AGAGGCCCAAGGCACAAGTCCAG (260) |
|  | LRMP_JA270_3 | ACATGCTTCAGGAGACTCTGTGGTTTCCC (261) |
|  | LRMP_JA270_4 | AGCCATCAATCAGGAAAGCCGGGTTAGTA (262) |
|  | LRMP_JA270_5 | GCTTCTCTAAACTCCAAGCCATCTTCTCTACGAAGAG (263) |
|  | LRMP_JA270_6 | GTGGGATGTCTCTTCAGTTTATGACACAATAGCTTCC (264) |
|  | LRMP_JA270_7 | ACTATTAGAGTCTTTAACACCTCTGTGTGAAGATGACA (265) |
| BCL6 | BCL6_HEX1 | AGGAGAGAAACCTTACCATTGTGAGAAGTGTAACCT (266) |
|  | BCL6_HEX2 | GGAAGTTTATTAAGGCCAGTGAAGCAGAGATGGTTT (267) |
|  | BCL6_HEX3 | AATAACATCGTTAACAGGTCCATGACGGGCTC (268) |
| PIM2 | PIM2_HEX1 | ACAGATCGACTCCAGGTGGCCATCAAAG (269) |
|  | PIM2_HEX2 | GCTGGTCCCCCTTGTCAGACTCAGT (270) |
|  | PIM2_HEX3 | CTACACTGACTTTGATGGGACAAGGGTGTACA (271) |
|  | PIM2_HEX7 | TCACATGCCCACTCGAAGTCGCA (272) |
|  | PIM2_HEX8 | CTGACTTTGATGGGACAAGGGTGTACA (273) |
|  | PIM2_HEX9 | CTGGTGCCCTGCTTCATGATGAACC (274) |
|  | PIM2_HEX10 | CACTGACTTTGATGGGACAAGGGTG (275) |
| ARID3A | ARID3A_FAM1 | AGCAGTTTAAGCAGCTCTACGAACTCGACG (276) |
|  | ARID3A_FAM2 | TGCAGAAGCGAGGGACACCTGTGA (277) |
|  | ARID3A_FAM3 | CCCTGCGGACCCAATACATGAAGTACCT (278) |
|  | ARID3A_FAM6 | CAACAGCCAAGCCTCCGAAAGCCG (279) |
|  | ARID3A_FAM7 | CGGCATCATGTACACAGGAGTTCTGTTTGCTCA (280) |
| CCND2 | CCND2_HEX1 | AGTTTGCCATGTACCCACCGTCGA (281) |
|  | CCND2_HEX2 | CTTTAAGTTTGCCATGTACCCACCGTCG (282) |
|  | CCND2_HEX3 | TTGCCATGTACCCACCGTCGATGAT (283) |
| FAM46C | FAM46C_JA270_1 | TTCTATTGCCCAGTTTCCCCAGCCAGAA (284) |
|  | FAM46C_JA270_2 | CTCTTCTATTGCCCAGTTTCCCCAGCCAG (285) |
|  | FAM46C_JA270_3 | CTCCTCTTCTATTGCCCAGTTTCCCCAGC (286) |
| TCF4 | TCF4_FAM1 | TCCTTCTTCATGCAAGATGGCCATCACAGC (287) |
|  | TCF4_FAM2 | AGGACCCTTACAGAGGCATGCCACC (288) |
|  | TCF4_FAM3 | TGGAGCAGCAAGTCCGAGAAAGGAATCTGAA (289) |
| JADE3 | JADE3_FAM1 | AGAAACCTGCTGAGGTATTCCGGAAGGAC (290) |
|  | JADE3_FAM2 | CACAGCCTTCTCTCAGGATTATAGCTGAGAAGGT (291) |
|  | JADE3_FAM3 | CTTGCAGAAATGGGTTGTGGGCCAGTT (292) |
|  | JADE3_FAM5 | TGTGTGCATCAGGCCTGCTATGGC (293) |
|  | JADE3_FAM6 | TGTGGATCCCAGAGGTCAGCATTGCTTG (294) |
|  | JADE3_FAM7 | AGGACCTGGAGAGGGTCCGAAATCTGT (295) |
|  | JADE3_FAM8 | CCAAGAAATTGATGCAGGGCTTCCTTTGACAAATG (296) |
| SSBP2 | SSBP2_FAM1 | CATGCCTAGTCCAGCAGATTCAACCAACTCT (297) |
|  | SSBP2_FAM2 | CCTGGACCTAACAGACCTAATTTTCCAATGGG (298) |
| PDK3 | PDK3_FAM1 | TTGAAGAATTCAATGCCAAAGCGCCAGACAAA (299) |
|  | PDK3_FAM2 | CGGATGTGGTGAAAGATGCATATGAAACAGCC (300) |
|  | PDK3_FAM3 | CAATTCCTGGACTTCGGGAGAGATAATGCATGTG (301) |
| ZNF318 | ZNF318_HEX1 | TGCTTCCCAGAAGCAAAAGGTTATTGAAGAGAGG (302) |
|  | ZNF318_HEX2 | TAACTGTTCCTGCAAAAGGCTCTGAGTTTCTGG (303) |
|  | ZNF318_HEX3 | CGGCTTCATAAACAACAAGGAGAAATGCTGCGC (304) |
| HMGN1 | HMGN1_HEX1 | CGAAGACTGAGGAGAGTCCAGCCTCT (305) |
|  | HMGN1_HEX2 | AACGAAGACTGAGGAGAGTCCAGCCTC (306) |
|  | HMGN1_HEX3 | AAGACTGAGGAGAGTCCAGCCTCTGATG (307) |
| FOXP1 | FOXP1_JA270-1 | CCACAAAAGATCAGTGGTAACCCTTCCC (308) |
|  | FOXP1_JA270_2 | TCCTATGCAAGCCGTGCATCC (309) |

TABLE 4 -continued

Probe sequences

| Gene | Probe_label | 5' to 3' Sequence (SEQ ID NO) |
|---|---|---|
| KIAA0226L | KIAA0226L_JA270_1 | TGTAGAAGATGTTCAGCGTGCAGGGCTT (310) |
| | KIAA0226L_JA270_2 | CATACAGTGGCTATGAAGGTTGTGCTGTGTTACA (311) |
| | KIAA0226L_JA270_3 | TGCAGCTCCTCTAAGAGTGTCACTTATGAGCC (312) |
| | KIAA0226L_JA270_4 | TGCAGCTGGCTCGATAGTCGTAAATGAAGA (313) |
| | KIAA0226L_JA270_5 | TTCATCCACCACTCAAGAGGGACCTTGTG (314) |

Validation of the 15-Gene Signature

The qRT-PCR classifier was validated in commercially acquired DLBCL FFPET specimens (validation cohort 2; n=29, and validation cohort 3; n=46). Concordance rate between qRT-PCR and Affymetrix microarray-based classifiers was 97.1% (Tables 5 and 6).

TABLE 5

Validation of qRT-PCR COO subtype classifier (Cohort 2, n = 29)

| | qRT-PCR COO classifier | |
|---|---|---|
| | ABC | GCB |
| Affymetrix | | |
| ABC | 7 | 0 |
| GCB | 0 | 18 |
| Unclassified | 1 | 3 |

TABLE 6

Validation of qRT-PCR COO subtype classifier (Cohort 3, n = 46)

| | qRT-PCR COO classifier | |
|---|---|---|
| | ABC | GCB |
| Affymetrix | | |
| ABC | 8 | 0 |
| GCB | 2 | 34 |
| Unclassified | 0 | 2 |

The high concordance of the DLBCL subtype classification signature in two independent DLBCL cohorts is surprising, especially given the relatively small number of genes in the signature. These results show that the DLBCL classifier can be used for quick-turn around, simple, inexpensive, and accurate determination of COO subtype.

Validation of the 6-Gene Signature

The qRT-PCR classifier with 6 of the genes was validated in commercially acquired DLBCL FFPET specimens (validation cohort n=50). The genes included in the 6-gene signature includes the ABC genes CCND2, FOXP1, and JADE3, and the GCB genes ZNF318, SSBP2, and PTK2. Concordance rate between qRT-PCR and Affymetrix microarray-based classifiers was 95% (Table 7).

TABLE 7

Validation of qRT-PCR COO subtype classifier (6-gene classifier)

| 6-gene COO classifier | Affymetrix | | | |
|---|---|---|---|---|
| | GCB | ABC | Unclassified | |
| GCB | 28 | 1 | 2 | n = 31 |
| ABC | 1 | 11 | 3 | n = 15 |
| Unclassified | 2 | | 2 | n = 4 |

The high concordance of a small 6-gene DLBCL subtype classification signature is surprising. These results show that the 6-gene DLBCL classifier can be used for quick-turn around, simple, inexpensive, and accurate determination of COO subtype.

We claim:

1. A method of providing treatment for an individual with diffuse large B cell lymphoma (DLBCL) comprising:
   (a) obtaining a sample from the individual (DLBCL sample);
   (b) detecting by qRT-PCR the expression of germinal center B cell (GCB) markers ZNF318, PTK2, SSBP2, and BCL6 in the DLBCL sample;
   (c) detecting by qRT-PCR the expression of activated B cell (ABC) markers ARIDA3A, CCND2, FOXP1, JADE3, and PIM2 in the DLBCL sample;
   (d) detecting by qRT-PCR the expression of a control gene in the DLBCL sample; and
   (e) providing treatment for the individual,
      (i) wherein the treatment comprises R-CHOP (rituximab or etoposide; cydophosphamide; doxorubicin; vincristine; and prednisolone) if the ratio of GCB marker expression to ABC marker expression is higher than a GCB threshold value; or
      (ii) wherein the treatment comprises an alternative therapy if the ratio of ABC marker expression to GCB marker expression is higher than an ABC threshold value.

2. The method of claim 1, further including detecting GCB marker LRMP in step (b) and detecting ABC markers TCF4 and FAM46C in step (c).

3. The method of claim 1, wherein the GCB threshold value is set based on the ratio of GCB marker expression to ABC marker expression in a GCB positive control.

4. The method of claim 1, wherein the ABC threshold value is set based on ABC marker expression to GCB marker expression in an ABC positive control.

5. The method of claim 1, wherein the sample is a from a lung biopsy or bronchoalveolar lavage.

6. The method of claim 1, wherein the sample is formalin-fixed paraffin embedded tissue (FFPET).

7. The method of claim 1, wherein the sample is blood, plasma, or serum.

8. The method of claim 1, wherein the detecting of (b) and (c) are carried out in multiplex in multiple vessels.

9. The method of claim 8, wherein each GCB and ABC marker is individually detected.

10. The method of claim 1, wherein the detecting of (b) is carried out in a single vessel for each sample.

11. The method of claim 1, wherein the detecting of Cc) is carried out in a single vessel for each sample.

12. The method of claim 1, wherein the detecting of (d) is carried out in the same vessel(s) as the detecting of (b) and (c).

13. The method of claim 1, wherein the alternative therapy includes a BTK inhibitor, SYK inhibitor, NFkB inhibitor, or immunomodulatory agent.

14. The method of claim 13, wherein the alternative therapy further includes R-CHOP.

15. The method of claim 1, comprising adjusting the level of expression detected for the genes in steps (b) and (c) based on the expression detected of the control gene in (d).

16. A kit comprising:
   (a) a mixture comprising a primer set and a fluorescently labeled probe that specifically amplifies and detects each of germinal center B cell (GCB) marker ZNF318, PTK2, SSBP2, and BCL6 gene products; and
   (b) a mixture comprising a primer set and a fluorescently labeled probe that specifically amplifies and detects each of activated B cell (ABC) marker ARIDA3A, CCND2, FOXP1, JADE3, and PIM2 gene products.

17. The kit of claim 16, wherein the mixture of (a) further includes a primer set and a fluorescently labeled probe that specifically amplifies and detects GCB marker LRMP and the mixture of (b) further includes a primer set and a fluorescently labeled probe that specifically amplifies and detects each of ABC markers TCF4 and FAM46C.

18. The kit of claim 16, wherein the mixtures of (a) and (b) each further comprise a primer set and a fluorescently labeled probe that specifically amplifies and detects a control gene product, wherein the fluorescently labeled probe that specifically detects the control gene product is differently labeled than the fluorescently labeled probes in mixture (a) and mixture (b).

19. The kit of claim 16, wherein the fluorescently labeled, probes in mixture (a) are all labeled with the same fluorescent label.

20. The kit of claim 16, wherein the fluorescently labeled probes in mixture (b) are all labeled with the same fluorescent label.

21. The kit of claim 16, further comprising reverse transcriptase and/or thermostable DNA polymerase.

22. The kit of claim 16, further comprising an enzyme with both reverse transcriptase and DNA polymerase activity.

23. The kit of claim 16, further comprising at least one control sample.

* * * * *